United States Patent [19]
Meador et al.

[11] Patent Number: 5,894,273
[45] Date of Patent: Apr. 13, 1999

[54] CENTRIFUGAL BLOOD PUMP DRIVER APPARATUS

[75] Inventors: James W. Meador, Houston; Byron C. Sutherland, Pearland; Joseph C. Kearns, Jr., Kingwood, all of Tex.

[73] Assignee: Fairway Medical Technologies, Inc., Houston, Tex.

[21] Appl. No.: 08/702,880

[22] Filed: Aug. 26, 1996

[51] Int. Cl.⁶ .......................... G08B 21/00; A61M 37/00
[52] U.S. Cl. ................. 340/606; 340/611; 604/4; 604/65; 128/DIG. 12; 128/DIG. 13
[58] Field of Search .................. 604/65, 66, 67, 604/4, 34, 30, 31, 131, 151; 128/DIG. 12, DIG. 13; 417/420, 360; 340/648, 606, 611, 618, 613, 619

[56] References Cited

U.S. PATENT DOCUMENTS

| | | | |
|---|---|---|---|
| H1324 | 6/1994 | Dalke et al. | 604/65 |
| 284,423 | 2/1883 | Holdsworth et al. | 417/28 |
| 4,079,007 | 3/1978 | Hutchisson | 210/85 |
| 4,083,777 | 4/1978 | Hutchisson | 210/22 A |
| 4,573,961 | 3/1986 | King | 604/6 |
| 4,778,445 | 10/1988 | Hubbard et al. | 604/4 |
| 4,821,028 | 4/1989 | Deckert et al. | 340/606 |
| 4,930,997 | 6/1990 | Bennett | 417/410 |
| 5,003,489 | 3/1991 | Wildberger | 340/606 |
| 5,021,048 | 6/1991 | Buckholtz | 604/151 |
| 5,147,186 | 9/1992 | Buckholtz | 417/420 |
| 5,186,431 | 2/1993 | Tamari | 604/4 |
| 5,394,739 | 3/1995 | Garvey, III et al. | 73/54.23 |
| 5,395,320 | 3/1995 | Padda et al. | 604/65 |
| 5,423,747 | 6/1995 | Amano | 604/65 |
| 5,437,634 | 8/1995 | Amano | 604/65 |
| 5,562,614 | 10/1996 | O'Donnell | 604/65 |
| 5,562,615 | 10/1996 | Nassif | 604/67 |
| 5,573,505 | 11/1996 | Johnson et al. | 604/65 |
| 5,609,576 | 3/1997 | Voss et al. | 604/67 |

OTHER PUBLICATIONS

Medtronic Bio–Console® 550 Extracorporeal Blood Pumping Console Operator and Reference Manual.
Bio Medicus Products Brochure.
Aires Centrifugal Pump System Brochure.
Pages marked "Sorin's Cardioplegia Console LCD Layout".

*Primary Examiner*—Jeffery A. Hofsass
*Assistant Examiner*—Van T. Trieu
*Attorney, Agent, or Firm*—Tim L. Burgess

[57] ABSTRACT

A centrifugal blood pump driver comprises a motor housing and the housing contains a motor for rotationally driving the centrifugal blood pump and a controller operatively associated with the motor for controlling the rotational speed of the motor; a speed selector for generating a selected speed signal signifying a selected rotational speed for the motor; sensors operatively associated with the motor or controller for sensing the rotational speed of the motor and outputting a monitor signal signifying such rotational speed; program memory for storage of a program of microprocessor readable instructions; a microprocessor under program control, in electrical connection with the controller, the speed selector, the sensor and the program memory, for receiving the selected speed signal and generating a speed control signal to the controller signifying the selected speed for the controller, and for receiving the monitor signal and outputting a display signal; a display in electrical communication with the microprocessor and responsive to the display signal for displaying information; motor housing circuitry for providing electrical communication among the controller, the speed selector, the sensor, the program memory, the microprocessor, and the display; and electrically conductive cable connected to the motor housing circuitry for transmitting electrical DC power to the motor housing circuitry from an external power source.

45 Claims, 40 Drawing Sheets

CENTRIFUGAL BLOOD PUMP DRIVER APPARATUS

FIELD OF THE INVENTION

This invention relates to an apparatus and method to drive a centrifugal pump which takes over or assists a patient's heart by pumping blood throughout his or her body.

BACKGROUND OF THE INVENTION

In open heart surgery, the heart and lungs are bypassed via a prosthetic or extracorporeal blood flow circuit so that the heart may be stopped and isolated for surgical repair. This extracorporeal blood flow circuit, popularly called a heart lung machine, contains the means to remove blood from the venous side of the patient, pump and oxygenate the blood, and return it to the arterial side of the patient. This circuit also has a variety of individual elements which perform certain functions such as heaters/coolers to elevate or decrease the temperature of the blood, components to add blood volume or cellular components, blood filters and so forth. These discrete elements of the circuit is interconnected by plastic tubing which, in turn, are connected to a patient completing the circuit. The means of pumping the blood throughout this bypass circuit has typically consisted of roller pumps. These roller pump work by rotating a mechanical arm which radially impinges and collapses a portion of the plastic tubing, one side of which is confined against a rigid semicircular wall. This action acts to propel the blood through the circuit. The flow rate of the blood is directly proportional to the rotary speed of the pump as this type of pump is a positive displacement device. Pumps of this type have been used for many years and are still the predominant type of blood pumping mechanism in use for open heart surgery.

Centrifugal pumps are small disposable devices and round in planar shape. These pumps typically have two compartments, a magnet compartment and a blood compartment. The magnet compartment is sealed and contains a bearing supported disk which contains a number of radially placed magnets. Coupled to the disk and protruding from the magnet compartment into the blood compartment is a shaft. Seals around the shaft prevent fluid from the blood compartment from entering into the magnet compartment. Attached to the shaft is an impeller which is contained within the blood compartment. Two tubes extend from the housing of the blood compartment.

An inlet tube extends axially from the blood compartment. An outlet tube extends orthogonal from the inlet tube and is located tangentially to the blood compartment. The pump is connected to the circuit by connecting the inlet connector of the pump to the inlet tubing of the prosthetic circuit and connecting the outlet connector to the outlet tubing of the prosthetic circuit. The circuit is then primed with fluid to remove air.

A disc similarly configured with magnets of opposite poles in it facing the magnets of the centrifugal pump is coupled to the shaft of a motor. This motor/disc system is then placed adjacent to the magnet disc of the pump. The magnets of the motor disc will attract the magnets of the pump disc and align themselves to each other. Energizing the motor will cause the motor/disc to rotate which, in turn, will cause the pump disc to rotate identically via the coupled magnets. This rotation also turns the shaft and the impeller of the pump as they are mechanically linked and blood is pumped. The centrifugal pump, unlike the roller pump, is not a positive displacement system, rather the centrifugal pump generates pressure which is converted into blood flow as a function of the downstream head of the system.

SUMMARY OF THE INVENTION

This invention in its basic aspect comprises a tetherable complete motor system comprising motive means adapted to connect to a centrifugal pump to rotationally drive the centrifugal pump and include a motor for rotationally driving the centrifugal pump and a controller operatively associated with the motor for controlling the rotational speed of the motor. Sensor means are operatively associated with the motive means for sensing the rotational speed of the motive means and outputting a monitor signal signifying such rotational speed. The motive and sensor means are included in a housing which contains speed selector means with a selector on the exterior of the housing for generating a selected speed signal signifying a selected rotational speed for the motor, internal program memory for storage of a program of microprocessor readable instructions, and microprocessor means under program control, in electrical connection with the controller, the speed selector means, the sensor means and the program memory, for receiving the selected speed signal and generating a speed control signal to the controller signifying the selected speed for the controller, and for receiving the monitor signal and outputting a display signal. The motor housing comprises display means in electrical communication with the microprocessor means and responsive to the display signal for displaying information and has motor housing circuitry means for providing electrical communication among the controller, the speed selector means, the sensor means, the program memory, the microprocessor means, and the display means. Electrically conductive cable means are connected to the motor housing circuitry means for transmitting electrical DC power to the motor housing circuitry means from an external power source. The external power source normally will be located in a separate console, and the cable means will serve as a tether to the console.

While not unique to simply provide an enclosed motor with a tethered cable to a perfusionist console, it is unique to provide a complete motor system with an on board microprocessor and speed selector which is detachable from a perfusionist console carrying the power source. Because the motor housing is detachable from a perfusionist console, the power cabled and tethered housing can be removed from the console and placed near to the patient. This flexibility of the motor/pump movement minimizes the length of the extracorporeal fluid circuit, and this benefits the patient.

The motor housing is suitably predominantly formed from extruded aluminum which has a high heat transfer capability. Extruding the aluminum also gives the ability to create geometric shapes within the housing with little cost impact and facilitates the exterior of the housing to have the capability to be pole mounted adjacent to the patient.

The motor system also contains volatile memory and a DC battery to provide power to the motor system volatile memory when power from the external source is absent. The microprocessor means on board the motor system and under program control from the program memory also includes means for recording unique identification of the motor and the controller and for cumulatively recording motor revolutions, for saving the cumulative revolutions to the motor system battery-backed volatile memory while power is supplied to the motor housing circuitry by the external source, and for reading the identification and cumulative revolutions from the motor housing memory after power is initially supplied to the motor housing circuitry on system startup. The volatile memory suitably is carried in the microprocessor, and as used herein, the expression "microprocessor" or "microprocessor means" comprehends a microprocessor with built in volatile memory as well as one without such memory. Reference herein to "volatile memory" may mean memory carried in a microprocessor or stand alone memory or both.

As mentioned, the motor system is suitably connected by power cable tether to a console. In accordance with an aspect of this invention, the console contains console display means for displaying information, and a power source. In this aspect, a unique feature of the detachable motor system of this invention is the display on the rear of the motor housing. The purpose of this display on the rear of the motor housing is to provide redundancy as well as basic operation indication if the motor system/pump is moved adjacent to the patient. In this manner, the eyes of the operator are not always required to be on the main display of the console to ascertain the instant condition of the system. Suitably with or without the console display embodiment, the information displayed by the display means responsive to the display signal is motor rotational speed (RPM's), although in accordance with this invention any of the displays described below may be employed where as more fully described below a console microprocessor is not also used. In the event a failure occurs, not only may console alarms be triggered, but also the display on the motor housing can provide additional visual and auditory indication of alarm conditions (suitably by blinking or changing colors or both).

This basic configuration is unique and carries several advantages. The first advantage is system safety. Redundancy or back up is a key in motor systems which are connected to a patient for support life. If the motor, motor controller or motor system microprocessor fail in some fashion, the motor system of this invention can be disconnected from a console to which it is tethered for power and replaced with another motor system. The battery backed memory of the microprocessor within the motor housing will note the motive system failure and preclude the motor housing from being attached to another console, by displaying an alarm, for example, flashing the display located at the rear of the housing and/or by disabling motive function. Since the memory of the resident microprocessor also records the life history of the components of the motor housing, notably the cumulative revolution hours of the motor (and controller) as well as its identification, this information is capable of being downloaded to the console and displayed on the below described graphics display of the console when the motor system is coupled to the console. Conversely, when a patient perfusion operation has ended, the resident motor system microprocessor (or as also described below, a console microprocessor) can update the microprocessor memory in the motor. Then if the motor system is subsequently uncoupled and moved to another console, the history of the motor system resides with the motor system.

In an aspect of this invention, the console includes circuitry means adapted to receive one or more input signals from one or more peripheral signaling sources adapted to sense a parameter of a patient connected in a blood flow circuit having an extracorporeal flow portion including a centrifugal blood pump, or a parameter of the extracorporeal portion of the circuit, or both. The inputs normally include input signals representing blood flow measurements and a selected patient or extracorporeal flow circuit temperature and selected extracorporeal flow circuit pressure. The electrically conductive cable means that comprises a tether power cable also includes conductors providing electrical communication between the motor system circuitry means and the console circuitry means. The motor system microprocessor means under program control—or in a different aspect involving dual microprocessors as more fully described hereinbelow, a console microprocessor means under program control—further includes means for interpreting the input signals from the one or more peripheral signaling sources and for outputting signals to the console display means to display information based on the input signals.

Another aspect of this invention is novel console displays. Console display means suitably include a plurality of function keys (switches) and a light screen responsive to the motor system microprocessor means under program control—or in a different aspect involving dual microprocessors as more fully described hereinbelow, a console microprocessor means under program control—to display screen images including (a) information and (b) menu options for calling different screens. The screen suitably comprises a liquid crystal display ("LCD") screen. The function buttons suitably are adjacent one margin of the LCD display. These correspond to selection legends on the LCD display or portions of the display that vary depending on a menu or display function chosen.

Suitably the console display comprises a front panel which is a silk-screened acetate circuit board and is adhesively backed and fitted to the frame of the front panel. This configuration makes the front panel splash proof. A portion of the front panel that is the backlit LCD graphics screen display allows substantial flexibility in the information that can be displayed as well as operator input flexibility. For example, this display can even be programmed in a variety of languages which, for example, can include even the graphics characters of Japanese and Chinese writing. Using a graphics LCD approach also allows different capabilities to be added to the invention by simply upgrading the firmware in the reprogrammable program memory rather than have to replace the entire console or a console circuit board or retrofit it with other hardware modifications.

The console panel display means suitably includes, alternatively, or in addition to the screen display, a scalar display of a predetermined original range of values and high limit that is automatically convertible a predetermined number of times by the microprocessor under program control to a predetermined different range of values and high limit when the next previous high limit is reached. The scaler display suitably comprises an array of light emitting diodes and associated drivers. Two circular arrays of light emitting diodes ("LED's") are suitably employed. The inside arc illuminates proportionally to the RPM of the pump and is suitably green in color. The outside row is suitably red in color and illuminates proportionally to pump flow in liters per minute ("LPM"). The purpose of these rows is to give a graphical indication of both flow and RPM and their relationship to one another. Suitably, two numeric LED displays are also furnished, color coded to match the graphical displays, e.g., a green RPM numeric display and a red numeric flow display.

The motor system microprocessor means under program control—or in a different aspect involving dual microprocessors as more fully described hereinbelow, a console microprocessor means under program control—further includes means for writing the information sent to the motor housing display and to the console display to the motor housing volatile memory while power from the external source is present.

Other novel aspects of this invention include the motor system microprocessor means under program control—or in a different aspect involving dual microprocessors as more fully described hereinbelow, a console microprocessor means under program control—further comprising means requiring speed selector means to be set to zero before the motor can be rotated, and further includes means for inputting a minimum speed at which the motor system microprocessor means under program control will ignore a the selected speed signal lower than the minimum speed and generate an alert signal that the selected speed is lower than the minimum speed. Means controllable by an operator after the alert signal is generated permit the microprocessor means under program control to produce the control signal at the selected speed signal lower than the minimum speed until motor speed is reset above the minimum speed or electrical power to the motor housing circuitry is discontinued.

Thus in one of the safety features of this invention, the front display panel also includes a low flow alarm and switch for the above program functions. Should the speed selector be accidentally be set to zero, the patient would be adversely affected. If the speed selector is set to zero, an alarm is activated and the motor/pump RPM is limited to an operator configurable threshold, say 2,000 RPM. To intentionally go below this value, the operator must push the button included on the front panel and the RPM will fall to the value set by the speed selector. This is important as the thresholds will be different in adult and pediatric cases, and is unique in this threshold being configurable by the operator using the microprocessor under firmware program control in the program memory.

This method therefore comprises setting a minimum value for motor rotational speed, generating a the selected speed signal signifying a desired motor rotational speed lower than a predetermined minimum value, maintaining the rotational speed of the motor at the minimum value upon receipt of the selected signal signifying a value lower than the minimum value, generating an alarm signal signifying that the selected signal is lower than the predetermined value, and optionally discontinuing the step of maintaining the rotational speed of the motor at the minimum value and allowing the motor to rotate at the speed signified by the selected speed signal or a selected other speed below the set minimum value.

The console suitably includes a power cord for receiving AC power, power supply means electrically connected to the console circuitry and the power cord for converting AC line voltage to DC voltage, at least one on-board DC battery, and a connector for an external DC power source both connected to the console circuitry. In another novel aspect of this invention, the motor system microprocessor means under program control—or in a different aspect involving dual microprocessors as more fully described hereinbelow, a console microprocessor means under program control— further comprises: means for determining what power is available from the console power sources comprising the power supply means, the on-board DC battery and the external DC power source connector, and if AC power is available, for determining whether it is 240 V, 120 V or 90 V and for auto-configuring the power supply means to accept the power available; means for prioritizing and distributing power such that if DC power is available from the console power supply means, it has priority, but if DC power is not available from the console power supply means and external DC power from the console external DC power source connector is available, then it has priority, but if both DC power from the console power supply means and from the console external DC power source connector are not available, then the on-board console battery has priority; and means for trickle charging the on-board console battery when DC power from the console power supply means is available.

The auto-configuring feature allows a single unit configuration to be manufactured and used worldwide, rather than having a technician manually configure the unit for the power requirements of the destination or importing country.

Suitably, secondary function panel display LED's are also optionally provided for the console, advantageously all in a same color, e.g., amber, that distinguishes these secondary parameters from the primary LED's of the console, e.g., flow being red and the RPM being green. These color separations are deliberate so that the operator can simply glance at the display and quickly ascertain the status of a particular function by knowing its color. An example of a secondary function includable on the front display panel is a plurality of timer displays. These timers have individual start and stop/reset buttons, to measure particular events of the procedure such as total time on pump. Another secondary function is a temperature display (also differently colored, suitably amber, from the primary flow and RPM functions) that displays temperature input from a temperature probe either in the patient or at a point in the extracorporeal flow circuit, for example near a heat exchanger. Another secondary function is a pressure display which measures pressure from a remote line to the patient, suitably in either mmHg or KPa. These pressure units can be set to the preference of the operator by using the menus on the LCD. Suitably also on the front panel display is an alarm mute button giving the operator in an alarm conditions the opportunity to mute the alarm by depressing this button. The alarm mute is then reset when the alarm condition ceases.

When the on-board console battery is used to power the console, suitably all the secondary amber LED's go out and only the lead LED's illuminate on the RPM and flow rings around speed selector. This is to save electrical power. (During battery operation as described in detail below the LCD carries a DISPLAY key that when depressed illuminates the numeric amber LED's for five seconds after the operator releases pressure from the switch. This default value is also changeable in the UTILITY menu.)

In the dual microprocessor aspect of this invention noted above, the console circuitry includes a console microprocessor means and console program memory and the console microprocessor is responsive to program instructions from the console program memory to interpret the input signals from the one or more peripheral signaling sources into information values and output signals to the console display means to display the input based information values or to perform one or more of the above tasks described where dual microprocessors may be used.

Where dual microprocessors are used, program memory for one is suitably non-volatile, e.g. an EPROM; the program memory for the other may be volatile, with the program being loadable to the volatile memory by a transfer of instructions from the non-volatile memory on system bootup. Preferably in such instance, the non-volatile program memory would reside in the console and the volatile program memory would be resident in the motor housing. This would eneable upgrades of software in all motors that are eventually connected to the console simply by reprogramming only the console non-volatile memory. If the single microprocessor design where the microprocessor resides only in the motor housing, the program memory is non-volatile. It is within the scope of this invention for program memory for both the console and motor housing microprocessors to be volatile and means provided to boot up and load the memory of one or both of them from a suitable permanent medium and medium reader such as a connected diskette and disk drive, but such complexity is un-necessary.

An advantage of using dual microprocessors is ability to assign to the console processor all processing duties except control of the motor controller, receipt of the monitor signal and output of the motor system display system.

In accordance with this advantage, this invention includes an aspect in which the speed selector means resides in the console, the microprocessor means in the motor system under program control is in electrical connection with the motor housing program memory and the console speed selector means (and as always, with the motor housing controller), for receiving the selected speed signal and generating a speed control signal to the controller signifying the selected speed for the controller. As always in this invention, the motor system includes display means in the motor housing in electrical communication with the motor housing microprocessor means and responsive to the display signal for displaying information. Power means are in the console for supplying a source of DC power, and circuitry means are in the motor housing and in the console and electrically conductive cable means interconnect the circuitry means for transmission of DC power to the motor housing circuitry means from the console power means and provide electrical communication between the console speed selector means and the motor system microprocessor means, motor housing program memory the controller, the sensor means, and the display means.

In an embodiment of the foregoing design where the speed selector means resides in the console, the console comprises a console microprocessor means under program control, in electrical connection with console program memory, the speed selector means, the sensor means, and the motor housing microprocessor means, for receiving the speed signal and the monitor signal and determining whether the monitor signal is within a predetermined limit of allowable variance of the speed signal, and if within the allowable limit, then outputting a display signal, but if outside the allowable limit under a predetermined sampling protocol, then outputting an alarm signal.

A method of controlling a centrifugal pump is accomplished by this structure. The method comprises generating a selected speed signal signifying a selected rotational speed for rotating a motor to rotationally drive the pump, interpreting the first signal and generating a speed control signal signifying the desired rotational speed output for a controller for controlling the motor, controlling the motor to rotate the motor according to the speed control signal, sensing the actual rotational speed of the motor and outputting a monitor signal signifying the actual rotational speed, checking the selected speed signal and the monitor signal and if the monitor value is within a predetermined limit of allowable variance of the speed signal, then outputting a display signal, but if the monitor signal is outside the limit, sampling the monitor and signal signals in a predetermined protocol and if the monitor signal remains outside the limit under the protocol, then outputting an alarm signal. and displaying the rotational speed of the motor responsive to the display signal or an alarm responsive to the alarm signal or displaying both the rotational speed and the alarm condition.

The screen images depicting information suitably include a MAIN screen displaying information which depends on whether the console is operating on line voltage or the console battery, and if operating on line voltage, then depicting information including: charge status of the on-board console battery, a histogram of pump flow in units of volume per minute over a period of time ending at current time, and one of a plurality of readouts including instantaneous pump flow (Q), blood flow per a patient weight unit (Q/wt) and blood flow per a patient body surface area unit (Q/BSA), but if operating on the console battery, then depicting information including: a notice that the battery is in use.

The screen images depicting options suitably include a MAIN screen displaying options which depend on whether the apparatus is operating on line voltage or the console battery, and if operating on line voltage, then depicting battery, pressure, flow indices and system options for calling respectively a BATTERY screen, a PRESSURE screen, a FLOW INDICES screen, and a SYSTEM screen, but if operating on the console battery, then depicting pressure, flow indices and system options for calling the PRESSURE screen, the FLOW INDICES screen, and the SYSTEM screen, and an illuminate display option.

The BATTERY screen is called upon keying a function switch operatively associated with the battery option on the MAIN screen, and depicts (a) battery status information including information based on the date of installation of the battery in the console, and (b) main and system options for calling respectively the MAIN or SYSTEM screens.

The PRESSURE screen is called upon keying a function switch operatively associated with the pressure option on the MAIN screen, and depicts at least (a) current calibration values for zero pressure and a high pressure alarms, and (b) pressure alert, zero transducer, main and system options for calling respectively PRESSURE ALERT or ZERO TRANSDUCER screens or the MAIN or SYSTEM screens, The PRESSURE ALERT screen is called upon keying a function switch operatively associated with the pressure alert option on the PRESSURE screen, and depicts (a) a high pressure alarm value readout, and (b) increase or decrease options for increasing or decreasing the high pressure alarm value, an OK option for accepting a high pressure alarm value, a zero transducer option for calling the ZERO TRANSDUCER screen, and system and main options for calling respectively the SYSTEM or MAIN screens.

The ZERO TRANSDUCER screen is called upon keying a function switch operatively associated with the zero transducer option on the SYSTEM screen, and depicts (a) an open to air zero pressure value readout, and (b) a set zero option for setting the open to air zero pressure value, an OK option for accepting a set open to air zero pressure value, and system and main options for calling respectively the SYSTEM or MAIN screens.

The FLOW INDICES screen is called upon keying a function switch operatively associated with the flow indices option on the MAIN screen, and depicts at least (a) values for height and weight of a patient, and (b) height, weight, Q/wt, Q/BSA and main options for calling respectively HEIGHT, WEIGHT, Q/WT, Q/BSA screens and the MAIN screen.

The HEIGHT screen is called upon keying a function switch operatively associated with the height option, and depicts (1) a default patient height value readout, and (2)increase or decrease options for increasing or decreasing the patient height value, an OK option for accepting a selected patient height value, and a main option for calling the MAIN screens.

The WEIGHT screen is called upon keying a function switch operatively associated with the weight option, and depicts (1) a default patient weight value readout, and (2) increase or decrease options for increasing or decreasing the patient weight value, an OK option for accepting a selected patient weight value, and a main option for calling the MAIN screens.

The Q/WT screen is called upon keying a function switch operatively associated with the Q/wt option, and depicts at least (1) the histogram and a Q/wt value readout, and (2)Q/BSA, height, weight, flow indices and main options for calling respectively a Q/BSA screen or the HEIGHT, WEIGHT, FLOW INDICES or MAIN screens, the MAIN screen containing the Q/wt value when called from the Q/WT screen.

The Q/BSA screen is called upon keying a function switch operatively associated with the Q/BSA option, and depicts at least (1) the histogram and a Q/BSA value readout, and (2)height, weight, Q/wt, flow indices and main options for calling respectively the HEIGHT, WEIGHT, Q/WT, FLOW INDICES and MAIN screens, the MAIN screen containing the Q/BSA value when called from the Q/BSA screen.

The SYSTEM screen is called upon keying a function switch operatively associated with the system option on the MAIN screen, and depicts at least (a) the histogram and one of the plurality of Q, Q/wt and Q/BSA readouts, and (b) alarms, status, battery, and main options for calling respectively ALARMS and STATUS screens and the BATTERY and MAIN screens.

The ALARM screen is called upon keying a function switch operatively associated with the alarm option on the SYSTEM screen, the ALARM screen depicting at least (a) the histogram and one of the plurality of Q, Q/wt and Q/BSA readouts, and (b) and low flow alarm, negative flow alarm, alarm volume and main options for calling respectively a LOW FLOW ALARM screen, a NEGATIVE FLOW ALARM screen, an ALARM VOLUME screen, or the MAIN screen.

The LOW FLOW ALARM screen is called upon keying a function switch operatively associated with the low flow alarm option, and depicts (1) a low flow alarm threshold value readout, and (2) increase or decrease options for increasing or decreasing the low flow alarm threshold value, an OK option for accepting a selected low flow alarm threshold value, and system and main options for calling respectively the SYSTEM or MAIN screens.

The NEGATIVE FLOW ALARM screen is called upon keying a function switch operatively associated with the negative flow alarm option, and depicts (1) a negative flow alarm threshold value readout, increase or decrease options for increasing or decreasing low flow alarm threshold values, an OK option for accepting a selected low flow alarm threshold value, and system and main options for calling respectively the SYSTEM or MAIN screens.

The ALARM VOLUME screen is called upon keying a function switch operatively associated with the alarm volume option, and depicts (1) a readout of alarm volume as a percent of maximum, increase or decrease options for increasing or decreasing the percentage of alarm volume maximum, an OK option for accepting a selected alarm volume percentage, and system and main options for calling respectively the SYSTEM or MAIN screens.

The STATUS screen is called upon keying a function switch operatively associated with the status option on the SYSTEM screen, and depicts (a) system status readouts including time, date, motor hours, cumulative motor revolutions, battery life and memory capacity of the motor assembly circuit board, and (b) utility, time-date, system and main options for calling respectively a UTILITY screen, a TIME-DATE screen, the SYSTEM screen, and the MAIN screen.

The motor system or console microprocessor memory under program control, according to the configuration as above described, also time tags and records alarm conditions. The console circuitry means advantageously includes a connector for a remote computer to make this data available through the connector, for example an RS-232 port on the console.

The UTILITY screen is called upon keying a function switch operatively associated with the utility option, and depicts communication, defaults and diagnostics options for calling respectively COMMUNICATION, DEFAULTS and DIAGNOSTICS screens, increase or decrease options for incrementing or decrementing to select one of the communication, defaults and diagnostics options, an OK option for accepting a selected the communication, defaults or diagnostics options, and system and main options for calling respectively the SYSTEM or MAIN screens. the COMMUNICATION screen is called upon keying a function switch operatively associated with the communication option, and depicts (1) a message to key an associated function switch when ready for a remote computer to receive data transfer from the apparatus, and (2) an OK option for initiating data the transfer, an abort option for canceling data transfer, and utility and main options for calling respectively the UTILITY or MAIN screens.

The DEFAULTS screen is called upon keying a function switch operatively associated with the defaults option, and depicts (a) default value readouts including a default time value for an illuminate display countdown when the apparatus is operating on the console battery and a default high pressure alarm value and (b) illuminate display countdown default and high pressure alarm default options for calling respectively an ILLUMINATE DISPLAY COUNTDOWN DEFAULT screen and a HIGH PRESSURE ALARM DEFAULT screen, increase or decrease options for incrementing or decrementing to select one of the illuminate display countdown default or high pressure alarm default options, an OK option for accepting a selected default option, and utility and main options for calling respectively the UTILITY or MAIN screens.

The ILLUMINATE DISPLAY COUNTDOWN DEFAULT screen is called upon keying a function switch operatively associated with the illuminate display countdown default option, and depicts (a) a default time value readout for the illuminate display countdown, increase or decrease options for increasing or decreasing the default time value, an OK option for accepting a selected default time value for the illuminate display countdown, a more option for calling a MORE screen, and utility and main options for calling respectively the UTILITY or MAIN screens.

The HIGH PRESSURE ALARM DEFAULT screen is called upon keying a function switch operatively associated with the high pressure alarm default option, and depicts (a) a default high pressure alarm readout for high pressure alarm, increase or decrease options for increasing or decreasing the default high pressure alarm, an OK option for accepting a selected default high pressure alarm, a more option for calling a MORE screen, and utility and main options for calling respectively the UTILITY or MAIN screens.

The MORE screen is called upon keying a function switch operatively associated with the more option, and depicts (a) default value readouts including a default low flow alarm value and a default negative flow alarm value and (b) low flow alarm default and negative flow alarm default options for calling respectively an a LOW FLOW ALARM DEFAULT screen and a NEGATIVE FLOW ALARM DEFAULT screen, increase or decrease options for incrementing or decrementing to select one of the low flow alarm default or negative flow alarm default options, an OK option for accepting a selected such default option, and utility and main options for calling respectively the UTILITY or MAIN screens.

The TIME-DATE screen is called upon keying a function switch operatively associated with the time-date option, and depicts, and depicts (a) readouts including a time of day value and a date and (b) time and date options for calling respectively an TIME screen and a DATE screen, increase or decrease options for incrementing or decrementing to select one of the time or date options, an OK option for accepting a selected time or date option, and system and main options for calling respectively the SYSTEM or MAIN screens.

The TIME screen is called upon keying a function switch operatively associated with the time option, and depicts (a) a time of day readout, increase or decrease options for increasing or decreasing the time of day readout, an OK option for accepting a selected time of day, and system and main options for calling respectively the SYSTEM or MAIN screens.

The DATE screen is called upon keying a function switch operatively associated with the date option, and depicts (a) a date readout, increase or decrease options for increasing or decreasing the date readout, an OK option for accepting a selected date, and system and main options for calling respectively the SYSTEM or MAIN screens.

DESCRIPTION OF THE DRAWINGS

The present invention may be more completely understood when taken in conjunction with the accompanying drawings, in which.

DESCRIPTION OF THE PREFERRED EMBODIMENT

Figure 1:
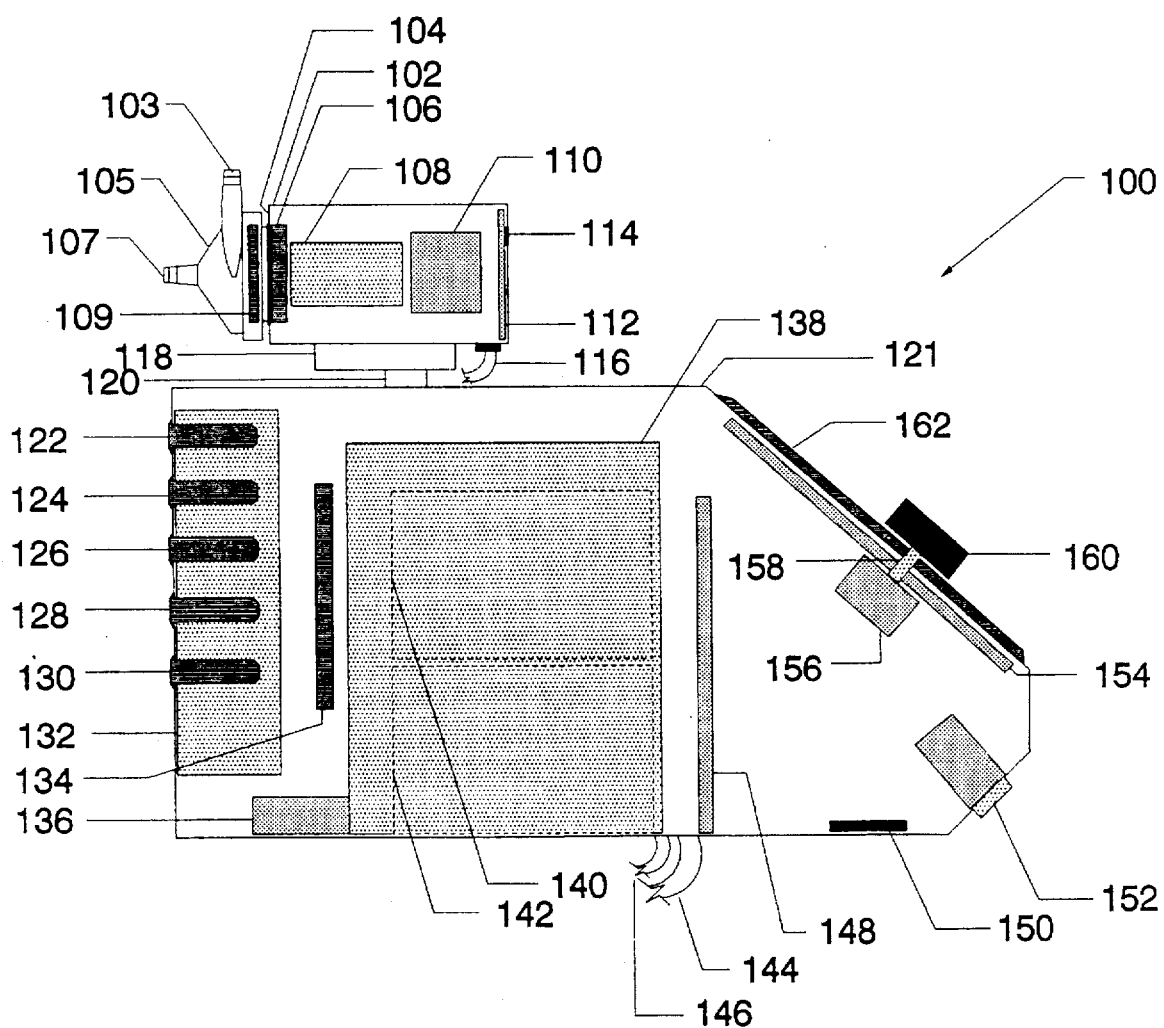
FIG. 1 is a sectioned side view schematic of the centrifugal pump driver illustrating the location of the interior components.

FIG. 1 illustrates a sectioned side view of the centrifugal pump driver system, generally shown by 100. The housing for the motor driver of the centrifugal pump is shown as 102 and 104 is the front of the housing where the disposable centrifugal pump 105 mechanically attaches and is magnetically driven by disc 106 which is mechanically linked to the motor 108. The motor controller 110 is electronically coupled to motor assembly 108 and provides the electrical signals necessary to drive the motor and also determines the RPM of the motor by monitoring the Hall effect sensors in the motor assembly 108. The circuit board which is electrically connected to the motor controller 110 is shown as 112. Circuit board 112 contains a microprocessor and a display 114 which is positioned to be viewable from the rear of the motor assembly 102. The circuit board 1 12 is also electrically connected to a cable 116 exiting the bottom of the motor assembly 102. This cable carries electrical power to the motor controller 110, and signals to the microprocessor and related circuitry on circuit board 112. This cable also carries information from the microprocessor on circuit board 112 to the console 121. The cable 16 is approximately 6' long and can be wrapped around a cord wrap (not shown) on the back of the console 121. The cable 116 has a connector on it which fits into the console 121 via connector 122 on the rear of the console 121. Console 121 has a plurality of connectors located on the rear of the console. Connector 124 is a connector for an ultrasonic flow probe. Connector 126 is a connector for a temperature probe. Connector 128 is a connector for electronic communications to a computer. Connector 130 is a connector for a 28 v DC input. Not shown is a leur connector which provides access to a pressure transducer located on circuit board 148. External electrical power is provided via power cord 144 which enters the bottom of console 121. The power circuit first goes to a power switch 152, then through a power filter (not shown) before it goes into a power supply 132 mounted to the rear of console 121. The power supply 132 converts the AC supply voltage to the appropriate DC voltages to operate the components within the system 100. There are two batteries 140 and 142 contained with console 121. These are two twelve volt batteries which are placed in series to yield 24 volts DC. A power distribution circuit board 134 takes input from the batteries 140 and 142, the power supply 132 which is fed from external power cord 144 and connections to the 28 volt power connector 130. The components on circuit board 134 determine what power is available and distributes it according to the circuit components. Circuit board 134 also prioritizes the power distribution. The first priority is AC power via the power cord, in this priority the electrical power is distributed and the batteries 140 and 142 are"trickle" charged to insure that they are at their peak. If AC power is not available then the second priority is the 28 volt inlet. Again, the circuits of the system 100 are supplied and batteries 140 and 142 are "trickle" charged. If AC nor external 28 v DC power is not available then internal batteries are used as the power source. This system examines the available power source(s) several times each second and sets the power configuration to the priority list just described as conditions warrant. Circuit board 138 is for conversion of the signals of the flow probe to flow information which can then be accessed by the microprocessor on circuit board 148. Circuit board 138 can be folded down for service once the case is removed from the console 121. Cooling for the console 121 is provided by a fan 136 located at the rear of the unit. Air inlet is provided by a grille 150 located near the front of the unit. The locations of the fan 136 and the grille 150 allow for air to be ducted through out the case and especially by the power supply 132 which generates the most heat within the unit. Circuit board 154 contains the circuitry necessary to drive the display of console 121 which also contains the LCD. Faceplate 162 is affixed to the front of the console and is also a circuit board. This faceplate has several switches on it and they are connected via a cable to the display circuit board 154. Faceplate 162 is sealed against the front of the console 121 and as such provides a splash proof enclosure. Knob 160 which extends from the faceplate 162 of console 121, controls the speed or RPM of the motor 108 and thereby the centrifugal pump. This knob 160 is connected to a shaft 158, which is part of a potentiometer 156 which is electrically connected to circuit board 154. Rotating knob 160 changes the electrical resistance of potentiometer 156 which, in turn, proportionally changes a reference voltage. As circuit board 154 is in electrical communication with circuit board 148 this reference voltage is monitored by the microprocessor located on circuit board 148 and by the microprocessor located on circuit board 112.

The microprocessor on circuit board 112 controls the output of motor 108 (and thereby the centrifugal pump) via the motor controller 110. The microprocessor on circuit board 144 monitors this action by checking the value of the potentiometer against the RPM of the motor, which is fed back by the motor controller 110. If these values are within predetermined limits then the microprocessor on circuit board 148 does nothing. If these values are outside predetermined limits then the microprocessor on circuit board 148 signals an error via the display circuit board 154 and its associated alarms and displays and resets the microprocessor on circuit board 112. If, after several reset attempts, the microprocessor on circuit board 112 does not again fall within predetermined limits, then the operator is requested to change motor housing assembly 102 complete with tethered cable 116 with a new assembly or disconnect the centrifugal pump on the front 104 of housing 102 and use a handcrank to maintain the patient until the subsystem can be replaced. This system provides the optimum redundancy. As the motor 106 and motor controller 110 are key and pivotal components, then in this configuration they are easily replaceable by simply disconnecting them via the connector which mates with connector 122 and replacing this subassembly by connecting a new subassembly into connector 122 and moving the centrifugal pump to the new motor assembly.

The microprocessor on circuit board 148 provides overall control of console 121 by monitoring and displaying Flow, RPM, Pressure, Temperature and providing the data and operating the LCD at the request of the operator.

Figure 2:
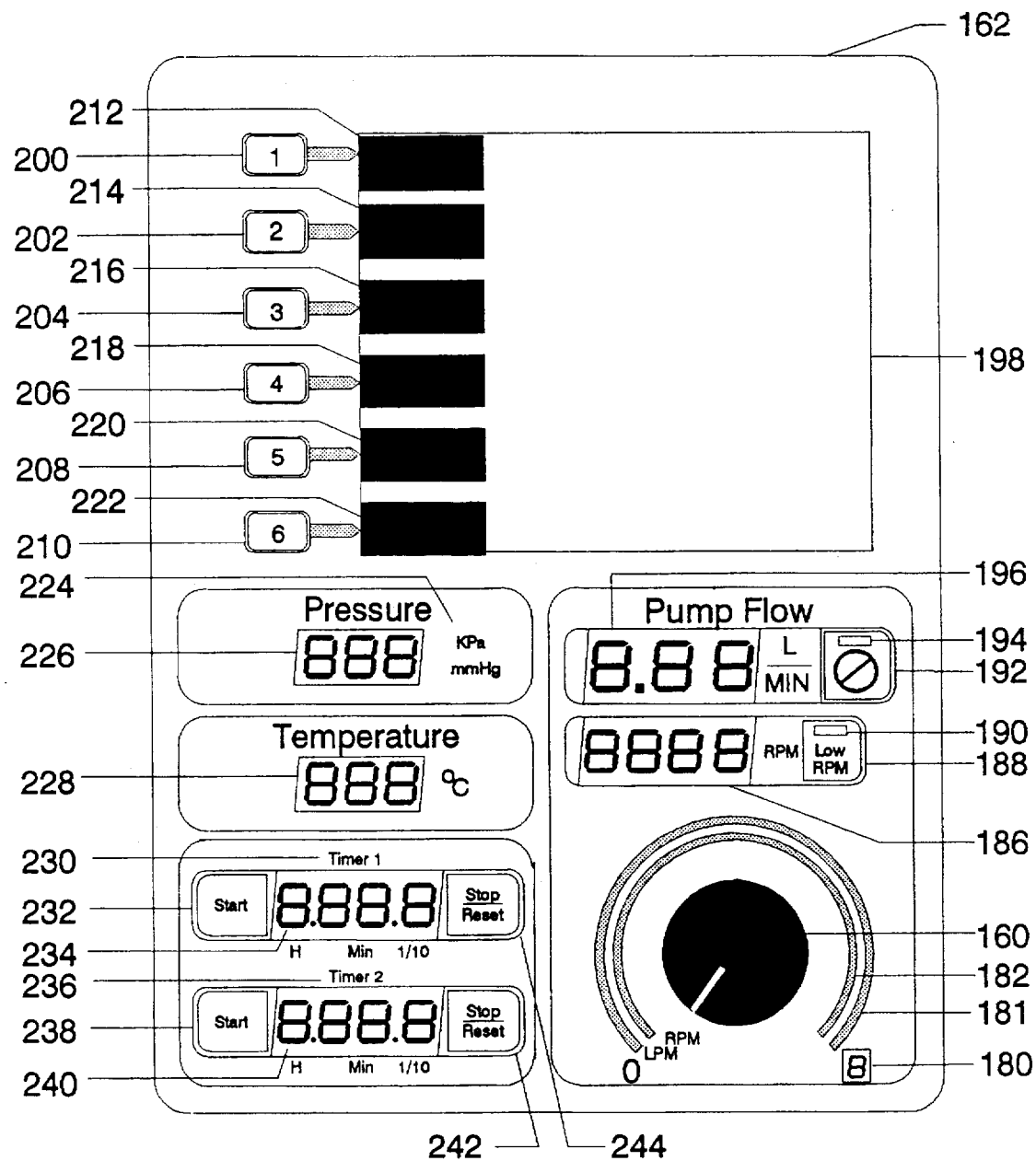
FIG. 2. is a front view of the operations panel of the centrifugal pump driver.

FIG. 2 is a front view of faceplate 162. Around control knob 160 is a ring 181 and a ring 182. Ring 182 is made up of a number of green light emitting diodes (LED's) which illuminate in proportion to the RPM of the motor 108 and therefore the centrifugal pump. Ring 181 is made up of red LED's which also illuminate in proportion to the Flow of the centrifugal pump in liters per minute. It is useful to relate the two graphical indicators to each other during the course of pump operation.

Display 180 is a single digit numeral comprised of a seven segment red LED. This number represents the high end of the Flow graphical ring and is programmed so that the ring is in units of 0–3, 0–6 or 0–9 Liters per minute. This automatic scaling reduces granular effects of the display in the low end if the scale were a constant 0–9 Liters per minute when the flow may be much nearer the low end, for example in pediatric cases.

The RPM numerical indication 186 is provided by four seven segment green LED's, the color of which matches the RPM flow ring 182. Adjacent to this display is a Low RPM switch 188 and indicator LED, 190. Should the knob 160 be inadvertently turned down below a preset threshold, for example 2,000 RPM, the microprocessor on circuit board 148 will sense this and instruct the microprocessor on circuit board 112 to maintain RPM at approximately 2,000 RPM. Simultaneously an audible alarm will sound and LED 190 will flash at approximately 1 second intervals. If the operator turns up the RPM above this threshold, or 2,000 RPM then the alarm condition will cease. If the operator wishes the RPM to be below this value then by pushing button 188 the alarm condition will cease and the RPM will fall to the set value of the knob. This feature exists for safety reasons. Pump flow in liters per minute is displayed by three, red, seven segment LED's 196. This color is also the same as the graphical flow ring 181. An audio alarm cancel button 192 is shown adjacent to the display. Its function is to mute audio alarms during any single given alarm condition. Once the alarm condition is cleared, this function reactivates. The LED 194 above this switch serves as a visual indicator of an alarm condition. The numeric pressure display 226 is made up of three, amber, seven segment LED's. Amber was chosen as an important yet somewhat neutral color for the numeric displays on the left side of the faceplate 162. In all cases, Flow is indicated in red and RPM is indicated in green. All other LED displays are amber, so that the operator may quickly glance and "fix" on the Flow and RPM parameters.

The units of pressure are in KPa, (Kilo Pascals) 224 or as shown immediately below this mmHg (millimeters of Mercury). Two LED's behind the faceplate 162 on circuit board 154 will either illuminate the KPa units or the mmHg units depending on the operator's choice as set through the LCD. The default setting is mmHg. Below the Pressure display is the Temperature display. The numeric display for temperature 228 is identical to that for pressure, carrying the same type and color of LED's. The displayed units for temperature is in degrees Celsius or ° C. Below the Temperature display are two timers. Timer 1,230 and Timer 2,236. Each of these timers have numerical displays 234 and 240 respectively which are amber, seven segment LED's. The first digit represents "hours" as reflected by the "H" below this character. The second two numbers are offset with periods and represent "minutes" as reflected by "Min" shown directly below these characters. The last numeral represents ⅒ minute or 6 seconds, which is reflected by the "⅒" directly below this number. Each timer has a start button 232 and 238 respectively and a Start/Stop button, 244 and 242 respectively. Pushing the start button activates the timer and pushing the Start/Stop button once stops the timer. If the Start button is again pushed then the timer continues. If the Start/Stop button is pushed twice in succession then the timer resets to a "0.00.0" display. Two timers are frequently used in pump procedures. The first frequently measures total "pump time" of a extracorporeal bypass case. The second timer measures special events of interest during the case.

To the top of faceplate 162 is the graphics LCD 198. To the left of this display are shown six displayed menu labels, 200, 202, 204, 206, 208, and 210 respectively from top to bottom. These software driven labels correlate to the six buttons shown to the side of the display or 212, 214, 216, 218, 220, and 222 respectively. The software is structured that different options may present themselves on the labels 212, 214, 216, 218, 220, and 222. Operator selection of these menu labeled items is accomplished by pressing the corresponding button or 200, 202, 204, 206, 208, and 210. Thus a menu label presented on label 220 can be selected by pressing button 208, or switch "5". This approach allows for extreme flexibility on the part of the software with minimum impact on the hardware.

Figure 3:
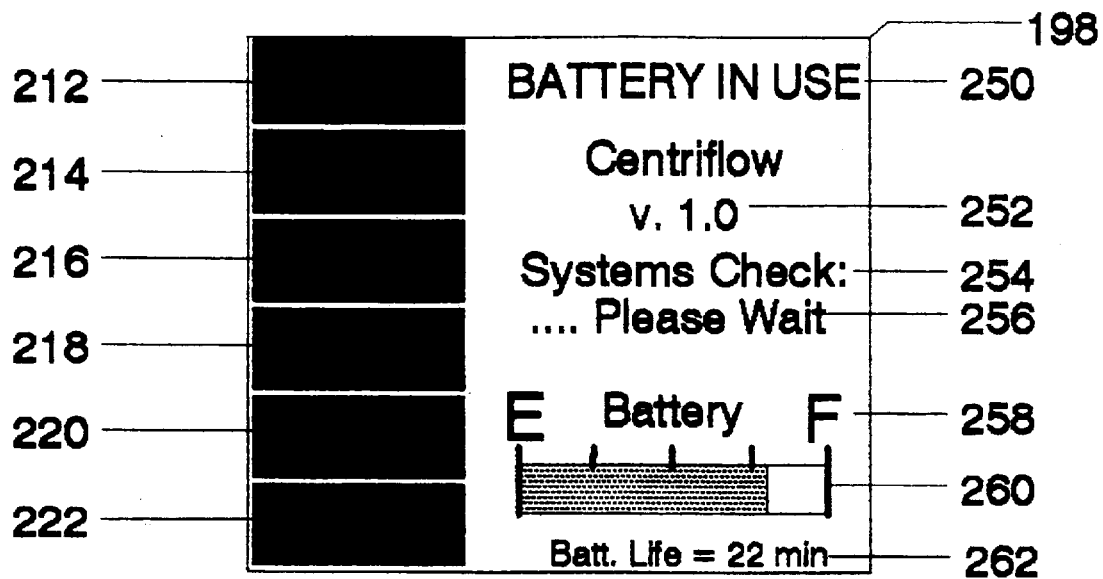
FIG. 3. is a view of the Start up Screen of the LCD on the operations panel of the centrifugal pump driver indicating that the internal systems are being checked.

FIG. 3 illustrates the display reading of the LCD 198. The menu legends 212, 214, 216, 218, 220 and 222 are blank. A "Battery in Use" message 250 is displayed only if the system is operating on battery power. This display will continually blink this message while the unit is operating on battery power. If the unit is operating with AC power then this message will not be displayed and 250 will be blank. The software version number 252 is displayed during this time period so that the operator can always verify the software version that the system is operating under. The "Systems Check" 254 message is displayed during the power up, as the software examines the components of the system 100 and determines that everything is operating correctly. Typically this examination takes approximately 10 seconds. The "Please Wait" message 256 is displayed during this portion of the circuit examination.

Figure 4:
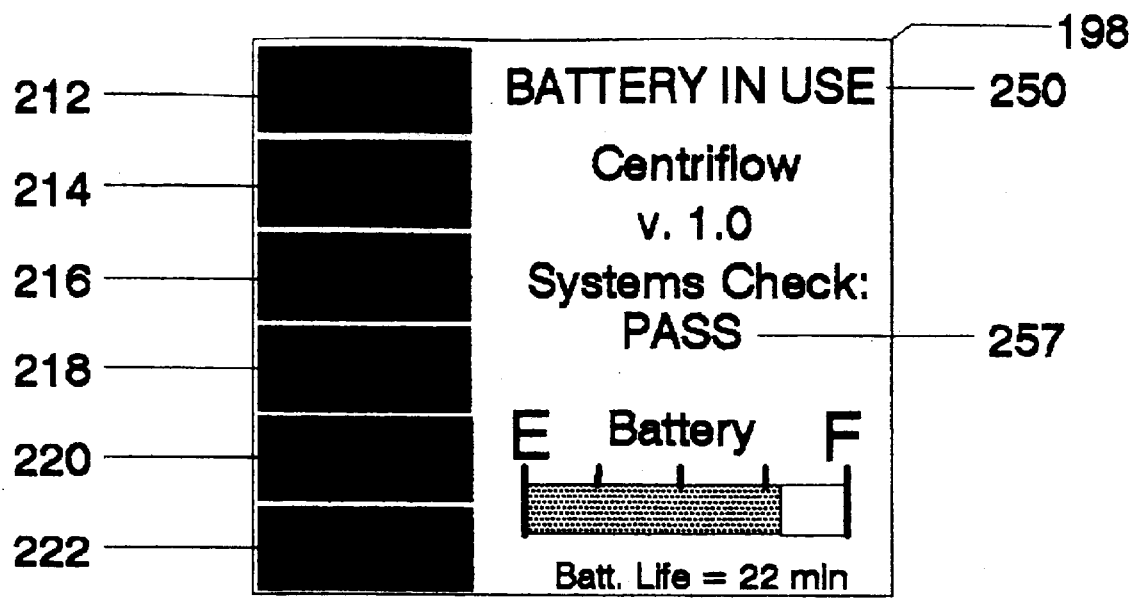
FIG. 4. is a view of the Start up Screen of the LCD on the operations panel of the centrifugal pump driver showing that the internal systems were checked and passed the examination.

FIG. 4 illustrates the second LCD 198. The message "PASS" is now displayed 257 is displayed, signifying that the system has examined the components of the console 100 and that everything was found to be in suitable working order. If the examination by the system found something in error then the message 257 would be replaced by "FAIL" and subsequent displays would detail the failures.

Figure 5:
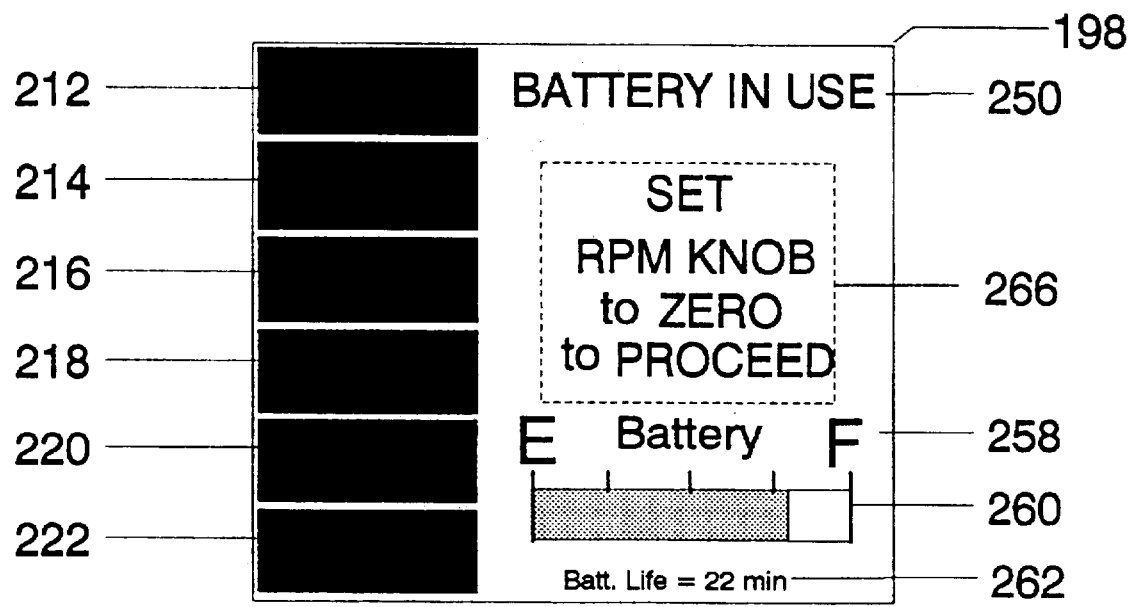
FIG. 5. is a view of the LCD on the operations panel of the centrifugal pump driver requesting that the RPM knob be turned to zero.
Figure 6:
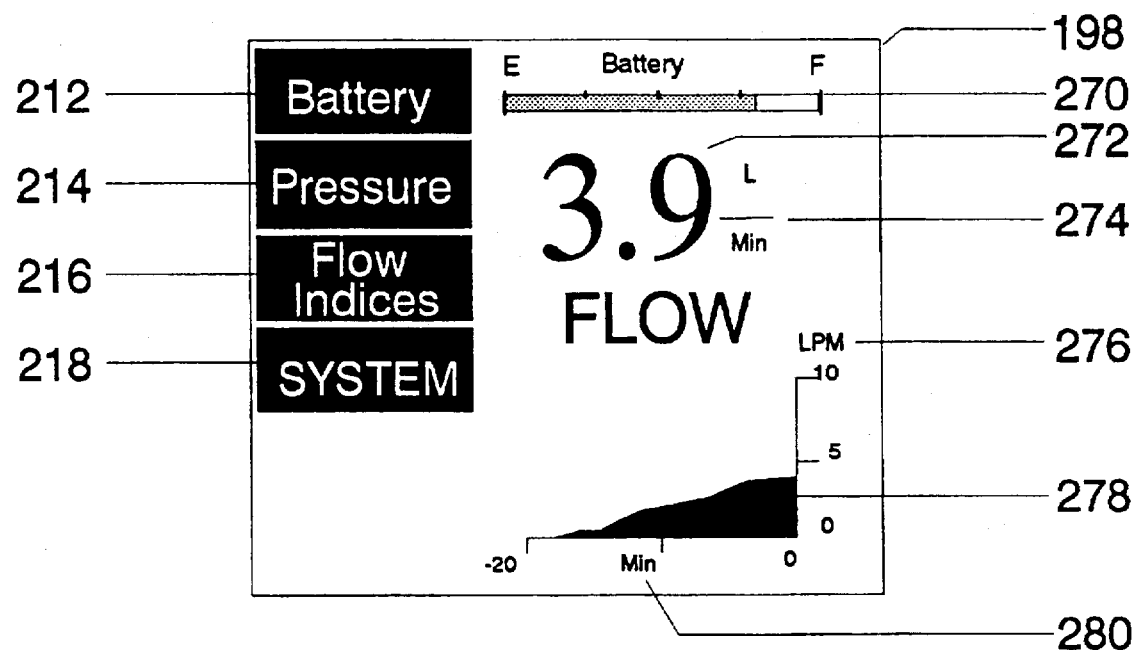
FIG. 6. is a view of the Main Screen of the LCD on the operations panel of the centrifugal pump driver.

FIG. 5 illustrates the next LCD display. The message in the box 266 tells the operator to "Set RPM Knob to Zero to Proceed". This message occurs if the RPM Knob 160 is not turned fully counter clockwise and is a safety concern. This forces the operator to start the pump from a stopped position. FIG. 6 illustrates the "MAIN" display if AC power is used and FIG. 7 illustrates the "MAIN" display if battery power is used.

FIG. 6 shows that menu legends 212, 214, 216 and 218 now have legends and the space occupied by legends 220 and 222 are blank. At the top of the display 198 is a battery indicator 270. This indicator occupies this top portion of the display for all displayed screens except when the batteries are used to provide power. Displayed in the format of a gasoline gauge, the operator can easily determine the approximate charge of the battery. In this illustration, the batteries are slightly more than ¾ charged. The flow of the pump as measured by the flowmeter and circuit 138 is displayed 272 and indicates "3.9", which would be identical to the reading of flow display 196. The units of flow are shown 274 and are expressed in L/Min or Liters per Minute. Below this display is a flow histogram 278. This is a graph which provides a flow history in Liters per Minute on the vertical axis 276 for the preceding twenty minutes on the horizontal axis 280. This histogram is useful for spotting trends which may be periodic in nature.

Figure 7:
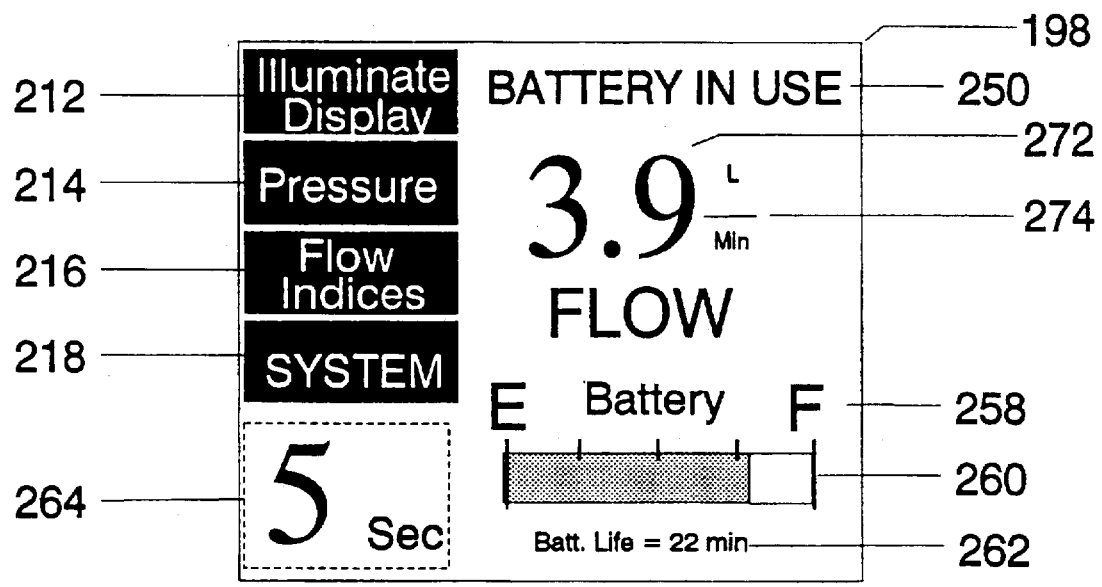
FIG. 7. is a view of the Main Screen of the LCD on the operations panel of the centrifugal pump driver when the console is being powered by batteries.

FIG. 7 illustrates the information on the display 198 which would be shown if the system 100 were operated by batteries. Changes of this display are that the small battery charge indicator 270 in FIG. 6 is replaced by a blinking "Battery in Use" message 250 in FIG. 7. This histogram 278 in FIG. 6 is replaced by an expanded battery charge indicator and legends 258, 260 and 262. While the system 100 is operated by batteries (refer to FIG. 2) the amber LED's 226, 228, 234 and 240 are not illuminated to save power. Additionally only the furthest clockwise LED on displays 182 and 181 are illuminated also to save power. During battery operation, Legend 212 displays "Illuminate Display", if switch "1" 200 is pushed to activate this function then all of the deactivated LED displays operate for a period of time after switch "1" 200 has been released. This period of time can be set by the operator, but the default time is 5 seconds. This time is displayed in countdown fashion in the lower left of display 198 indicated by 264. This allows the operator to take pressure 226, temperature 228 and timer 234 and 240 data as needed with minimal compromise on the battery life.

Figure 8:
FIG. 8. is a view of two of the label legends on the LCD showing their alternate blinking between two labels.

Sometimes, as one patient case has ended, the operating room will be set up for the next case. As a result the console system 100 will not be turned off rather it will remained powered waiting for the next case. In this event, if the pump motor has been idle for a predetermined period of time, yet power is maintained to the console 100 then the patient data will not be current for the subsequent case. Consequently the system 100 will determine how much time has elapsed since the pump was turned off. If this elapsed time period exceeds a certain value or a default then the operator may need to be reminded to change the patient parameters of height, weight and pressure zeroing (the purpose of these parameters will be explained later). To accomplish this operator notification process FIG. 8 illustrates the legend keys for Pressure 214 and Flow Indices 216. On the Main Display such as FIG. 6 these legends 214 and 216 will blink alternately. The Pressure legend will illustrate alternately between 214 and 215 as shown in FIG. 8 so that the message is to "Check Pressure". Similarly, the Flow Indices legend will blink alternately between 216 and 217, as shown in FIG. 8 to yield the message "Check Flow Indices".

Figure 9:
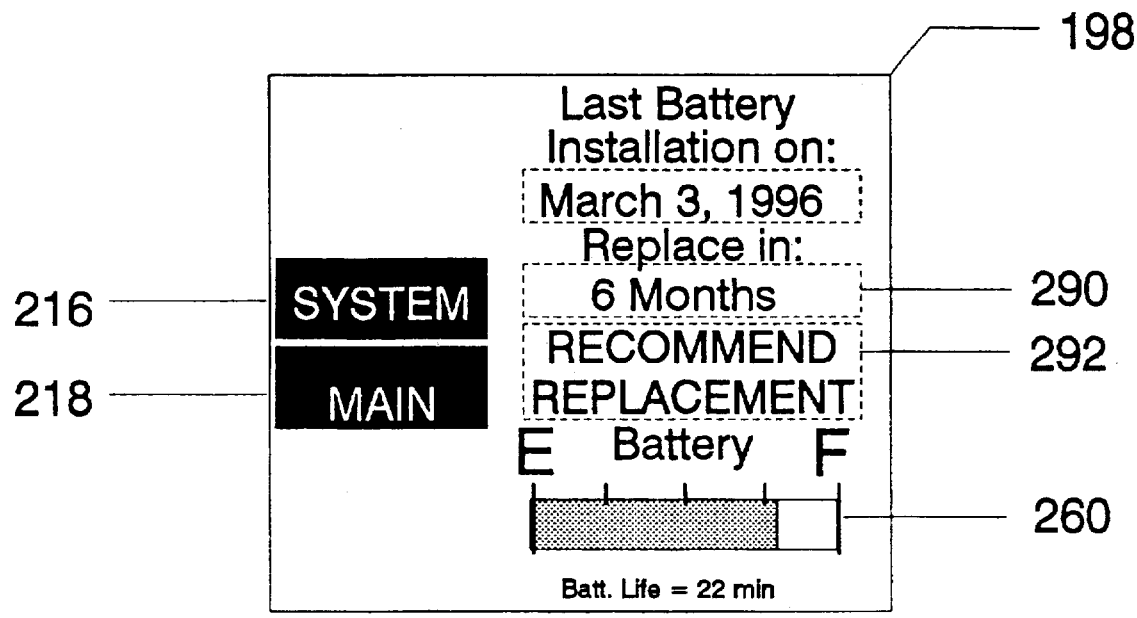
FIG. 9. is a view of the Battery Screen of the LCD on the operations panel of the centrifugal pump driver.

FIG. 9 illustrates the resultant display if switch "1" 200 is pressed when legend 212 illustrates "Battery" as depicted in FIG. 6. In this figure only legends 216 and 218 have printed information on them which is "System" and "Main" respectively. If switch "3" 204 is pressed while "System" is displayed on legend 216, then the display 198 will switch to the System menu reflected in FIG. 20. The "Main" legend is always displayed on each display menu so that the operator may quickly return to the "Main" menu, in this case by pressing switch the corresponding switch. In the case of FIG. 9 pressing switch "4" 206 which corresponds to the legend 218 containing "Main" will cause the system to return the display 198 to the "Main" menu as indicated by FIG. 6 for AC power. In FIG. 9, the top of the display indicates that the last battery installation occurred on Mar. 3, 1996. This date information is retained by the memory of the system when the batteries were actually replaced. Below this information, is a recommendation of when the batteries should again be replaced "6 Months" 290. This information is continually updated via a real time clock resident in the console. Should this recommendation time be sufficiently short or if this time has been exceeded then the message "Recommend Replacement" 292 will also be displayed. The battery information 260 is displayed to the lower portion of the display 198.

Figure 10:
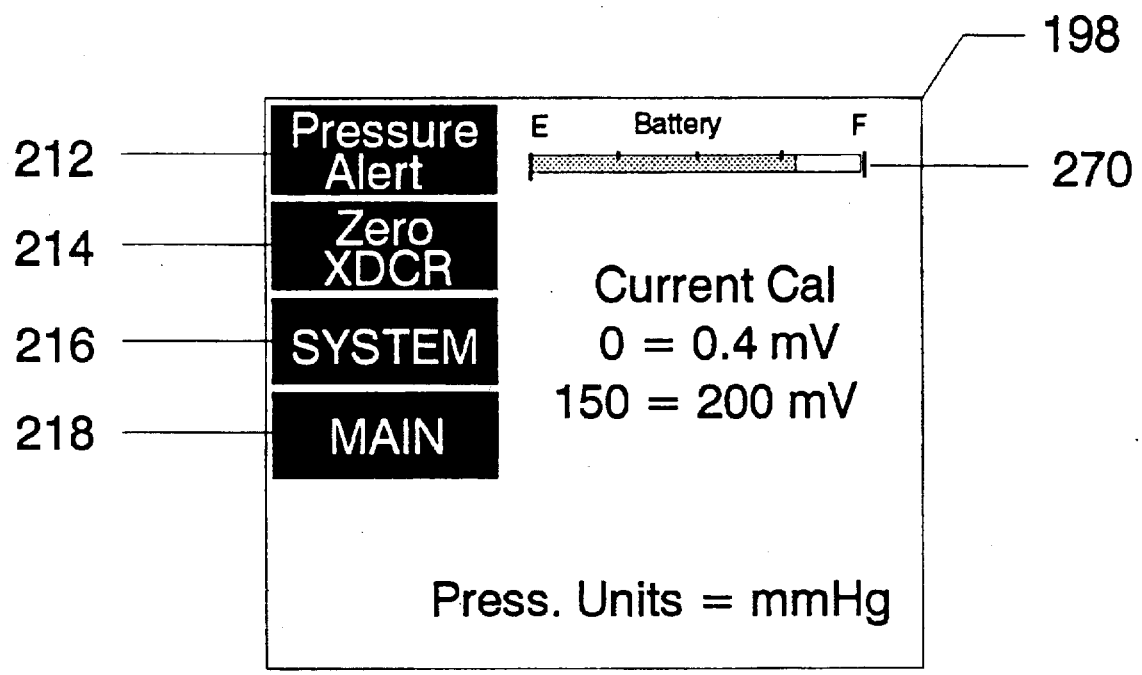
FIG. 10. is a view of the Pressure Screen of the LCD on the operations panel of the centrifugal pump driver.

FIG. 10 illustrates the display 198 if switch "2" 202 is pressed while "Pressure" is displayed in legend area 212 as in FIG. 6. FIG. 10 has four menu legends. Legend 212 has a label of "Pressure Alert" which provides for Alarm thresholds, legend 214 has a label of "Zero Xducer" which provides for zeroing the pressure transducer, legend 216 has a label of "System" which transfers the menu to the "System" menu to be described later and legend 218 has the label "Main" which transfers the menu to the "Main" menu described previously. The top of the display 198 carries the battery indication 270. Below the battery indication 270 are information lines. The "Current Cal" is the pressure transducer calibration header. The next line indicates "0 =0.4 mv" which is the millivolt (mv) reading for zero pressure, determined by calibration. The next line is "150=200 mv" which is the millivolt reading of the pressure transducer at a pressure of 150 mmHg. The last line is a statement that the units of pressure are in "mmHg" or millimeters of Mercury. The units of pressure options are mmHg or KPa (Kilo Pascals) which are selectable in another menu option. If switch "1" 200 is pressed which corresponds to label 212 carrying the legend "Pressure Alert" then the display 198 is represented by FIG. 11.

Figure 11:
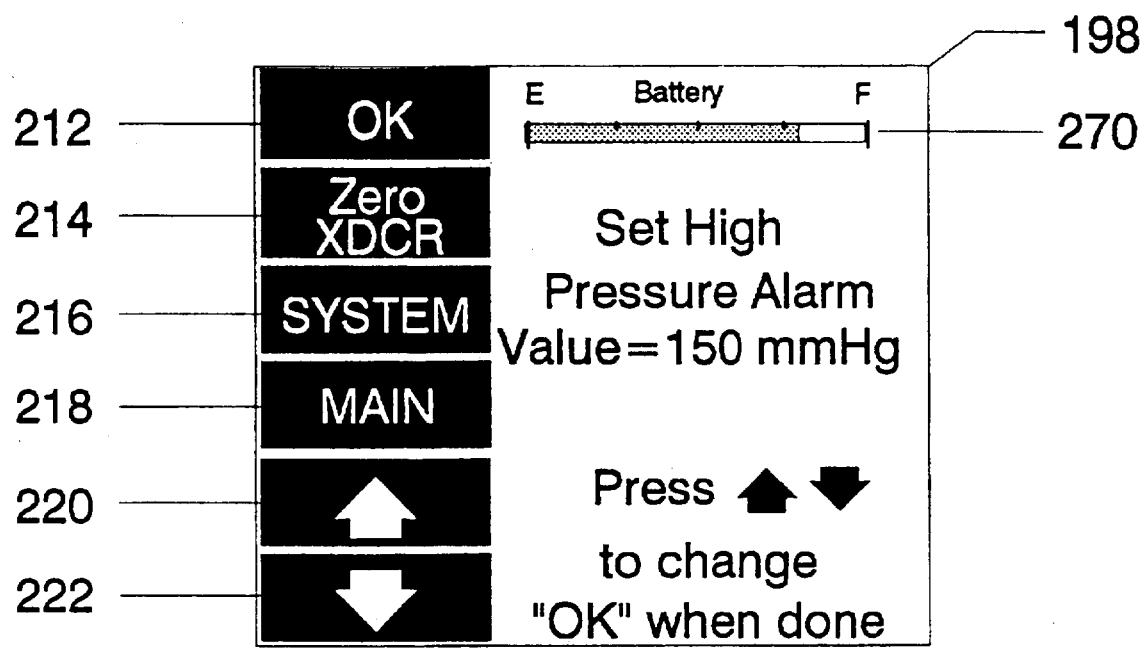
FIG. 11. is a view of the High Pressure Alarm Screen of the LCD on the operations panel of the centrifugal pump driver.

FIG. 11 shows the Pressure Alert screen and its function is to set the alarm threshold for high pressure. Legend label 212 is "OK", legend label 214 is "Zero XDCR", legend label 216 is "System", legend label 218 is "Main", legend label 220 is an up or increasing arrow, and legend label 222 is a down or decreasing arrow. Below the battery indicator 270 is the text "Set High Pressure Alarm" which indicates the function of the display which is to set the upper pressure threshold for the pressure alarm. The next line is "Value=150 mmHg". This indicates that the current alarm threshold is 150 mmHg. If, during use, the pressure exceeds this value then the alarm will sound. At the bottom of the display 198 are instructions: "Press (up arrow, down arrow) to change 'OK' when done". If the operator wants to increase this threshold then the up arrow, legend label 220 corresponding to switch "5" 208 can be pressed by the operator and the threshold values will be increased accordingly and displayed on display 198. Similarly, by pressing switch "6" 210 which corresponds to label legend 222 which illustrates the down arrow, the pressure alarm threshold will decrease and be reflected by the change in the number on the display 198. Once the operator is satisfied with the alarm threshold, then switch "1" 212 is pushed which corresponds to the legend label "OK" which tells the computer that the selection is complete. The computer stores this new value as the pressure alarm threshold.

Figure 12:
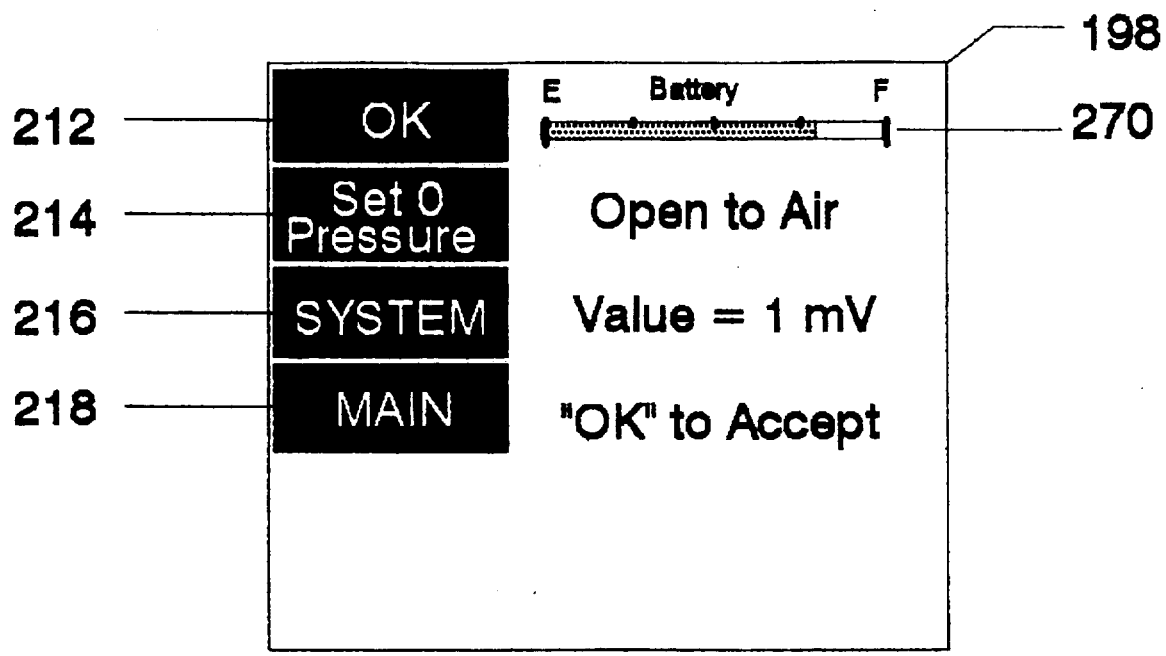
FIG. 12. is a view of the Zero Transducer Screen of the LCD on the operations panel of the centrifugal pump driver.

FIG. 12 illustrates the display 198 if the "Zero XDCR" function, switch "2" 202 label legend 200 of FIG. 10 (or FIG. 11). The function of this display is to zero the pressure transducer. Below the battery indicator 250 are three text lines. The first "Open to Air" is instructional, telling the operator to open the transducer to air. The second line "Value=1 mv" states that the current voltage value of the pressure transducer is 1 mv or 1 millivolt, this will obviously change with the transducer and pressure conditions and the operator will be expecting a suitable range of values. As the operator sets the height of the pressure line to the patient, this 1 mv value will also change. Once the operator is satisfied with the orientation of the pressure line then "OK"

label legend 212 represented by switch "1" 200 will be pushed and the computer will store this mv (millivolt) value as the zero reference for the pressure transducer.

FIG. 6 is the reference figure for the "Main" display where another menu option will be explored. Pressing switch "3" 204 corresponding to label legend 216 which carries the function "Flow Indices" in FIG. 6 will yield the display illustration represented by FIG. 13.

Figure 13:
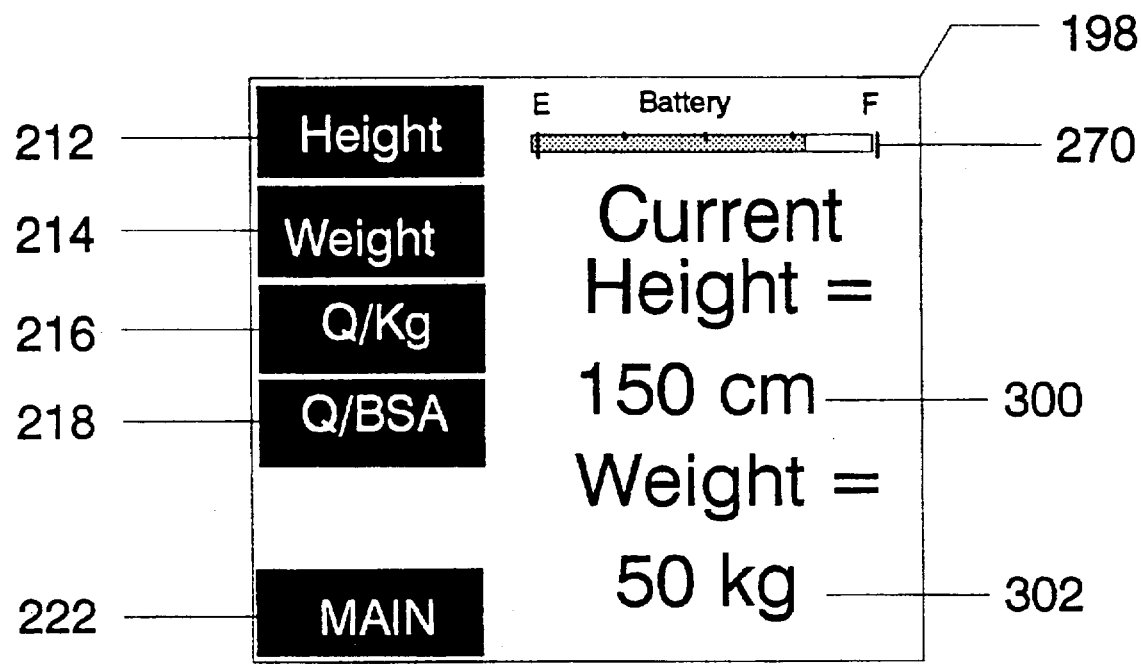
FIG. 13. is a view of the Flow Indices Screen of the LCD on the operations panel of the centrifugal pump driver.
Figure 14:
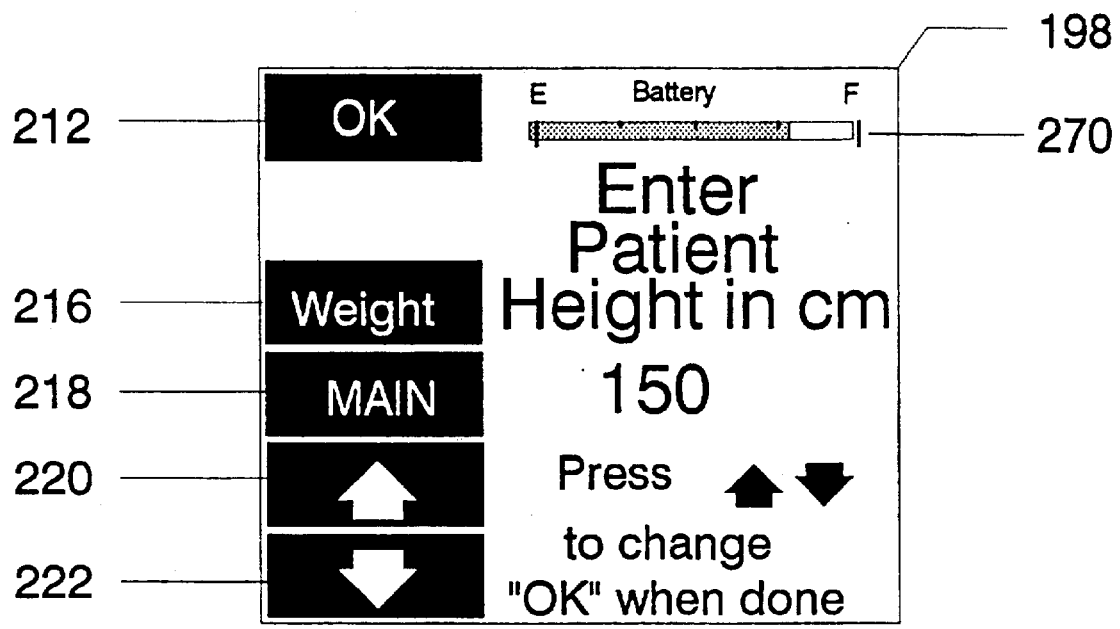
FIG. 14. is a view of the Screen to set the patient height of the LCD on the operations panel of the centrifugal pump driver.
Figure 15:
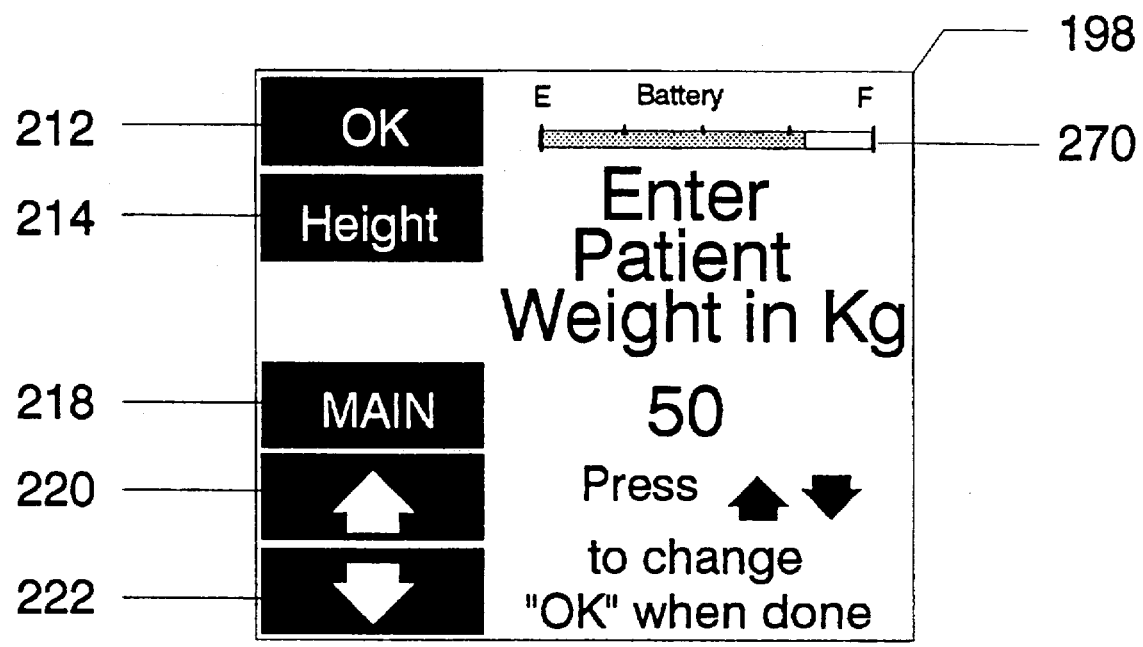
FIG. 15. is a view of the Screen to set the patient weight of the LCD on the operations panel of the centrifugal pump driver.

The purpose of this menu as shown in FIG. 13 is to enter the patient height and weight so that flow per unit weight (label legend 216 "Q/Kg") or flow per body surface area (label legend 218 "Q/BSA") may subsequently be calculated and be offered as a display option on the "Main" menu (272, 274 of FIG. 6) In FIG. 13, below the battery indicator 250 are two basic statements on the display. The first is "Current Height=150 cm". This represents the default value of the current height of the patient or 150 cm (centimeters). The second statement is "Current Weight=50 Kg". This represents the default value of the current weight of the patient or 50 Kg (Kilograms). If the operator wishes to change the patient height then switch "1" 200 is pressed, representing label legend 212 which states "Height". The resultant display illustration 198 by undertaking this function is represented by FIG. 14. If the operator wishes to change the patient weight then switch "2" 202 is pressed, representing label legend 214 which states "Weight". The resultant display illustration 198 by undertaking this function is represented by FIG. 15. Again of note in FIG. 13 is that the label legend 208 states "Main" so that simply pressing switch "6" 210 which corresponds to this legend, the operator is returned to the "Main" menu (FIG. 6).

FIG. 14 illustrates the FIG. 13 option described above where the operator presses switch "1" 200, representing label legend 212 which states "Height". This display screen states "Enter Patient Height in cm" below the battery level indication 270. The number illustrated "150" is a default value. As in a prior menu the operator instructions are at the bottom of the display. "Press (up arrow, down arrow) to change 'OK' when done". If the operator wants to increase the value of the height then the up arrow, legend label 220 corresponding to switch "5" 208 can be pressed by the operator and the height value in centimeters will be increased accordingly and displayed on display 198. Similarly, by pressing switch "6" 210 which corresponds to label legend 222 which illustrates the down arrow, the height value will decrease and be reflected by the change in the number on the display 198. Once the operator is satisfied with the alarm threshold, then switch "1" 212 is pushed which corresponds to the legend label "OK" which tells the computer that the selection is complete. The computer stores this new value as the patient height value. The value 300 in FIG. 13 will then be updated to the height selection just made by the operator. Legend 216 carries the label "Weight" which refers to changing the Patient Weight menu to be described next, and the legend 218 carries the "Main" menu label discussed earlier.

FIG. 15 illustrates the FIG. 13 option described above where the operator presses switch "2" 202, representing label legend 214 which states "Weight". This display screen states "Enter Patient Weight in kg" below the battery level indication 270. The number illustrated "50" is a default value. As in a prior menu the operator instructions are at the bottom of the display. "Press (up arrow, down arrow) to change 'OK' when done". If the operator wants to increase the value of the weight then the up arrow, legend label 220 corresponding to switch "5" 208 can be pressed by the operator and the weight value in centimeters will be increased accordingly and displayed on display 198. Similarly, by pressing switch "6" 210 which corresponds to label legend 222 which illustrates the down arrow, the height value will decrease and be reflected by the change in the number on the display 198. Once the operator is satisfied with the weight value threshold, then switch "1" 212 is pushed which corresponds to the legend label "OK" which tells the computer that the selection is complete. The computer stores this new value as the patient weight value. The value 302 in FIG. 13 will then be updated to the weight selection just made by the operator. Legend 216 carries the label "Height" which refers to changing the Patient Height menu previously described, and the legend 218 carries the "Main" menu label discussed earlier.

Referring back to FIG. 13, the next options are "Q/Kg" reflected by legend 216, activated by depressing switch "3" 204 and "Q/BSA" reflected by legend 218, activated by depressing switch "4" 206. If the patient height and weight values are current, then FIG. 16 is displayed if the "Q/Kg" option is chosen and FIG. 17 is displayed if the "Q/BSA" option is chosen.

Figure 16:
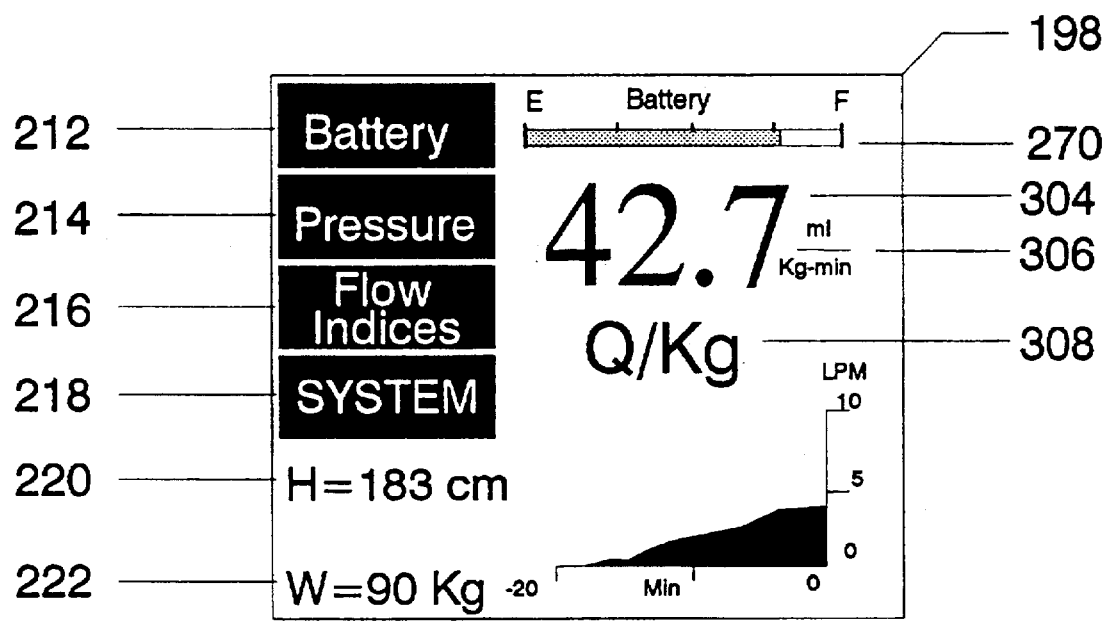
FIG. 16. is a view of the Main Screen of the LCD on the operations panel of the centrifugal pump driver showing flow in Q/Kg.

FIG. 16 is a simple variant of the Main display, FIG. 13. The difference is that the units of flow are in "ml/Kg-min" 306 and is simply the previous flow in Liters per minute, multiplied by 1,000/Patient Weight in Kg this result is shown 304. These units are useful for "normalizing" the flow of the patient based on the size of the patient. The display 198 also indicates, in large letters, that the screen indicates flow in units of "Q/Kg" 308. The values for the height "H" and weight "W" are also shown to the lower left of the display 198 occupying the space of legends 220 and 222. This will be the "new" Main display until other flow indices are selected. The numeric display of pump flow 196 remains at the "Liters per Minute" value.

Figure 17:
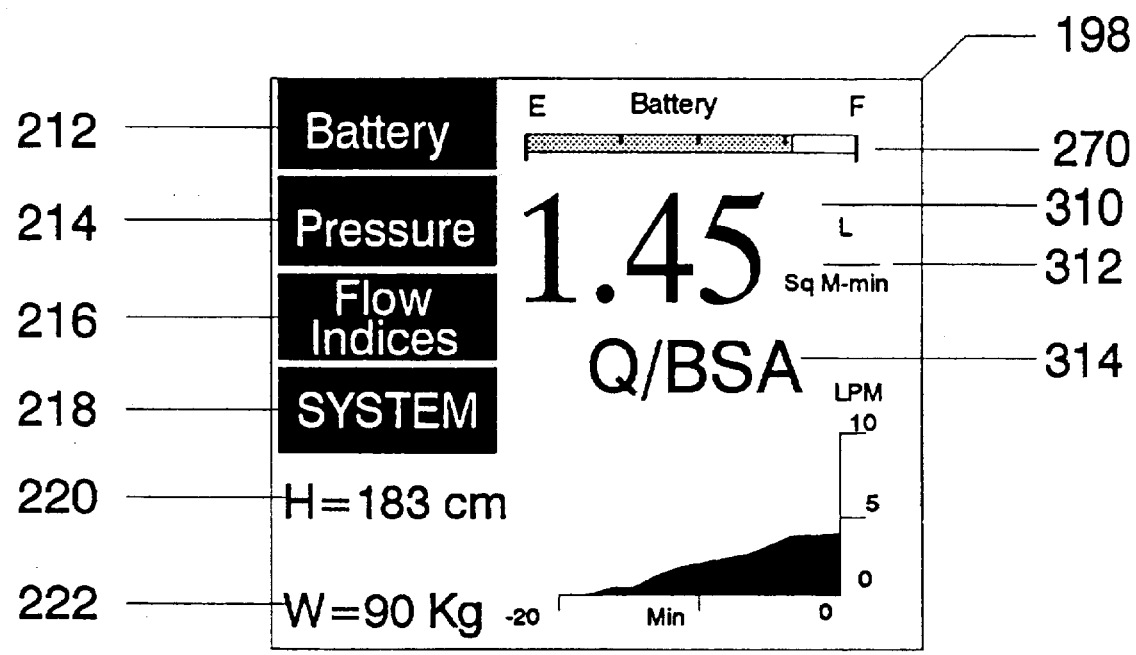
FIG. 17. is a view of the Main Screen of the LCD on the operations panel of the centrifugal pump driver showing flow in Q/BSA.

FIG. 17, like FIG. 16 is a simple variant of the main display, FIG. 13. The difference is that using the patient height and weight, the body surface area (BSA) is calculated and shown as 310. Flow is displayed as "ml/Sq M—min" or milliliters per square meter—minute 312 and the "Q/BSA is also shown in large letters 314. Q/BSA is also known as the cardiac index. The values for the height "H" and weight "W" are also shown to the lower left of the display 198 occupying the space of legends 220 and 222. This will be the "new" Main display until other flow indices are selected. The numeric display of pump flow 196 remains at the "Liters per Minute" value.

Figure 18:
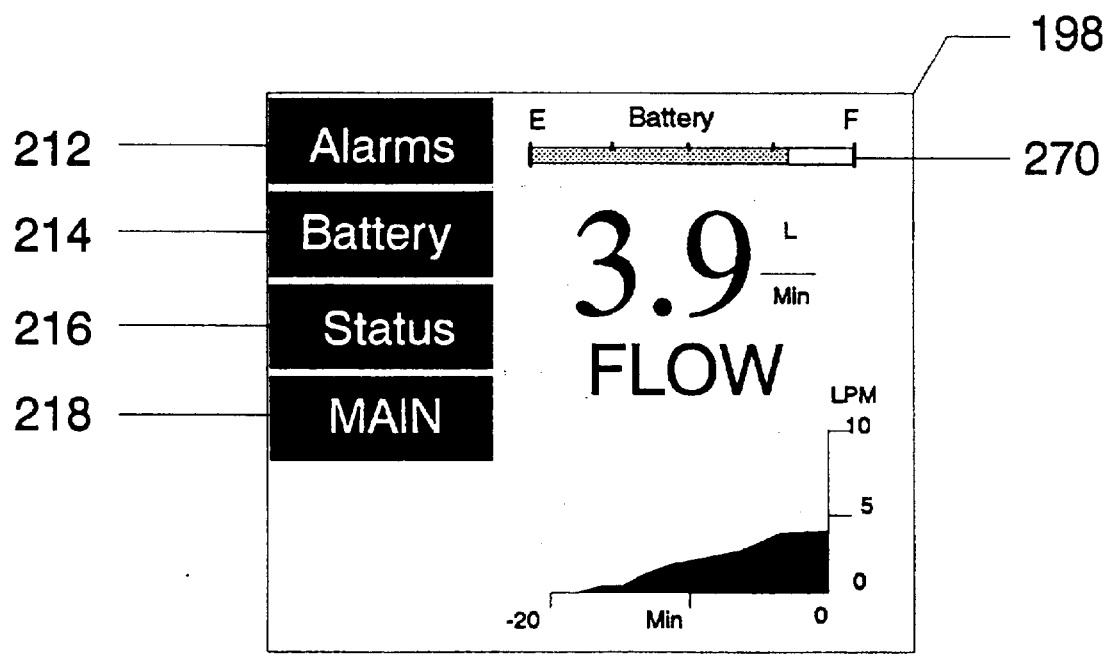
FIG. 18. is a view of the System Screen of the LCD on the operations panel of the centrifugal pump driver.

Returning back to FIG. 6, the "Main" screen, switch "4" 206 can be pushed to activate the "SYSTEM" menu which is the label for legend 218. FIG. 18 is the result of this switch activation.

FIG. 18 is the same as FIG. 6 except for the legend labels, 212, 214, 216 and 218. These labels are now "Alarms", "Battery", "Status" and "Main" respectively. "Battery" and "Main" have been previously discussed. Pressing switch "1" 200 corresponding to label legend 212 "Alarms" will activate the display 198 to indicate FIG. 19.

Figure 19:
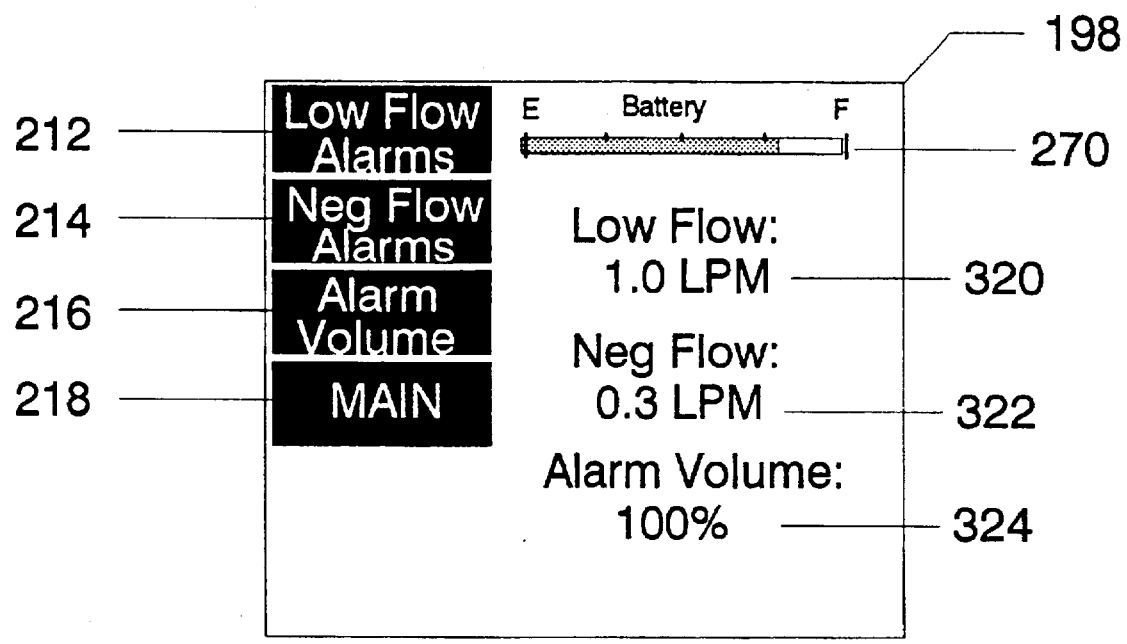
FIG. 19. is a view of the Alarms Screen of the LCD on the operations panel of the centrifugal pump driver.

FIG. 19 carries the label legends, "Low Flow Alarms" 212, "Neg Flow Alarms" 214, "Alarm Volume" 216 and "Main" 218. The activation of the "Main" routine has already been discussed. Below the battery indication 270 in FIG. 19 are the status' of the Low Flow Alarm as 1.0 LPM or Liters per Minute, the Neg. Flow Alarm or 0.3 Liters per Minute, and the Alarm Volume 100% Each of these three items are shown with the default values and are similarly changed. To choose to set the value of the "Low Flow Alarms" switch "1" 200 is pushed which corresponds to label legend 212 or "Low Flow Alarm". This changes the display to that of FIG. 20.

Figure 20:
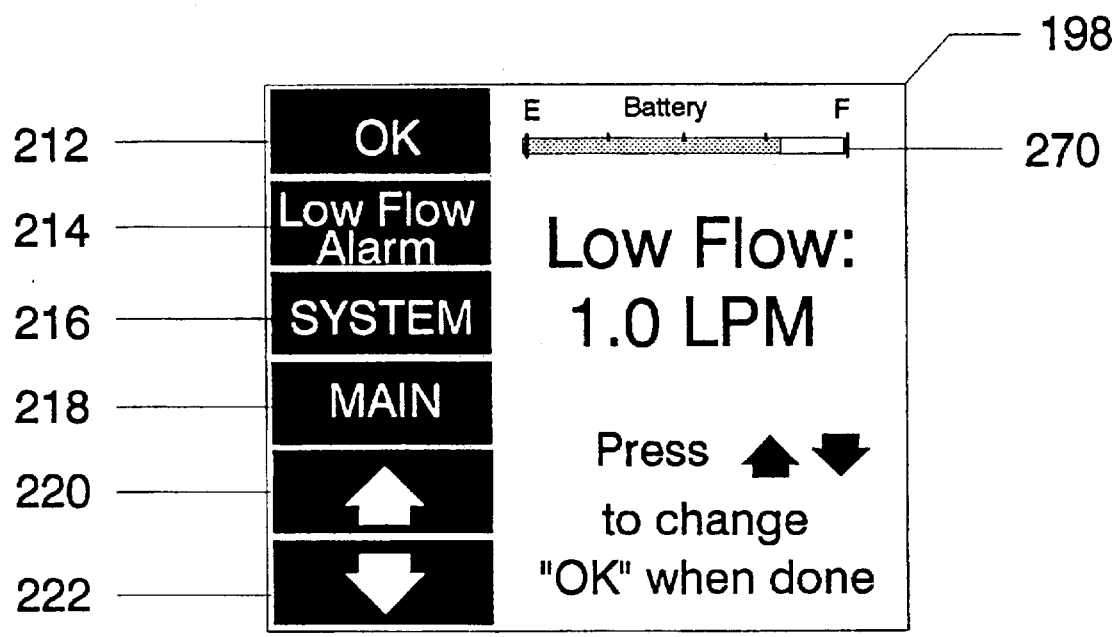
FIG. 20. is a view of the Low Flow Alarms Screen of the LCD on the operations panel of the centrifugal pump driver.

The display screen in FIG. 20 states "Low Flow: 1.0 LPM" below the battery level indication 270. The number illustrated "1.0" is a default value. The operator instructions are at the bottom of the display. "Press (up arrow, down arrow) to change OK when done". If the operator wants to increase the value of the Low Flow Alarm then the up arrow, legend label 220 corresponding to switch "5" 208 can be pressed by the operator and the alarm value in LPM will be increased accordingly and displayed on display 198. Similarly, by pressing switch "6" 210 which corresponds to label legend 222 which illustrates the down arrow, the alarm value will decrease and be reflected by the change in the number on the display 198. Once the operator is satisfied with the alarm threshold, then switch "1" 212 is pushed which corresponds to the legend label "OK" which tells the computer that the selection is complete. The computer stores this new value as the new Low Flow Alarm value. The value 320 in FIG. 19 will then be updated to the height selection just made by the operator.

In FIG. 19 the "Neg Flow" or Negative Flow Alarm is similarly changed as the Low Flow Alarm just described. To choose to set the value of the "Neg Flow Alarms" switch "2" 202 is pushed which corresponds to label legend 214 or "Neg Flow Alarm". This changes the display to that of FIG. 21.

Figure 21:
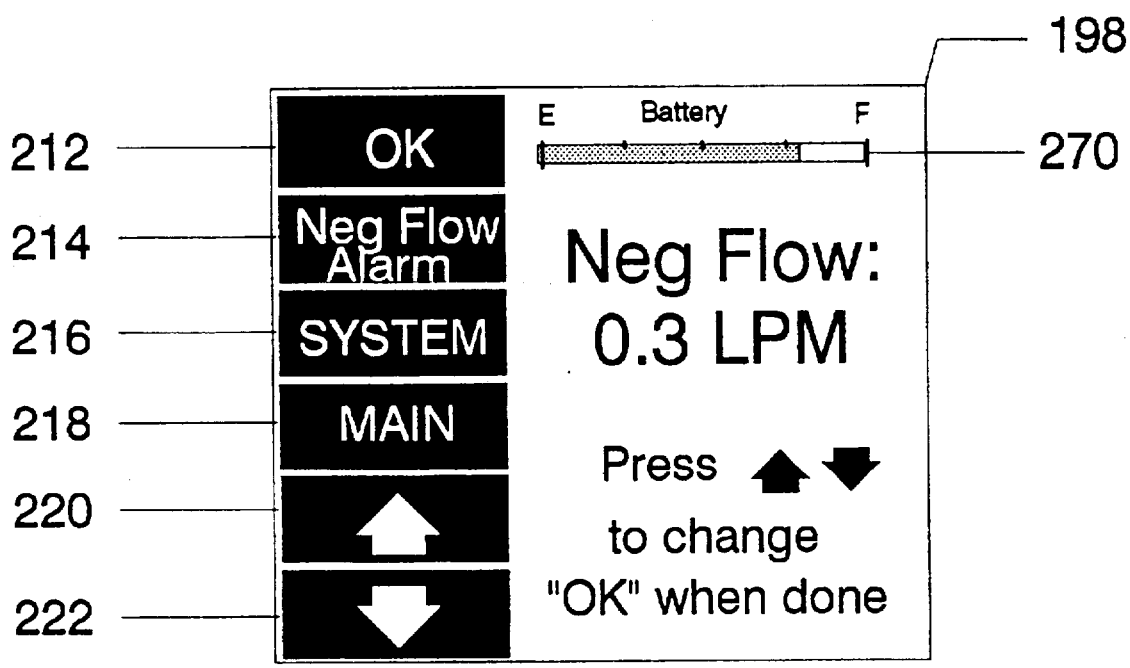
FIG. 21. is a view of the Negative Flow Alarms Screen of the LCD on the operations panel of the centrifugal pump driver.

The FIG. 21 display screen states "Neg Flow: 0.3 LPM" below the battery level indication 270. The number illustrated "0.3" is a default value. The operator instructions are at the bottom of the display. "Press (up arrow, down arrow) to change OK when done". If the operator wants to increase the value of the Low Flow Alarm then the up arrow, legend label 220 corresponding to switch "5" 208 can be pressed by the operator and the alarm value in LPM will be increased accordingly and displayed on display 198. Similarly, by pressing switch "6" 210 which corresponds to label legend 222 which illustrates the down arrow, the alarm value will decrease and be reflected by the change in the number on the display 198. Once the operator is satisfied with the alarm threshold, then switch "1" 212 is pushed which corresponds to the legend label "OK" which tells the computer that the selection is complete. The computer stores this new value as the new Neg Flow Alarm value. The value 322 in FIG. 19 will then be updated to the height selection just made by the operator.

In FIG. 19, the "Alarm Volume" is changed from the default value by pushing switch "3" 204 which corresponds to label legend 216. This changes the display to that of FIG. 22.

Figure 22:
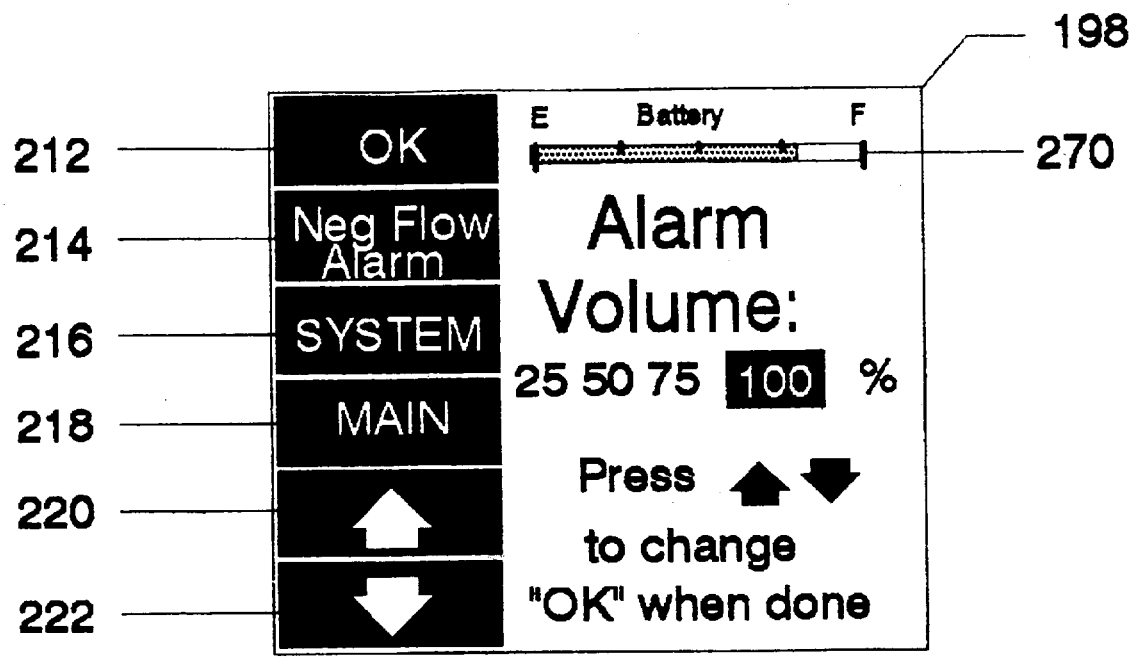
FIG. 22. is a view of the Alarm Volume Screen of the LCD on the operations panel of the centrifugal pump driver.

The FIG. 22 display screen 198 states "Alarm Volume:" and then four values, 25%, 50%, 75% and the highlighted 100% below the battery level indication 270. The highlighted 100% is a default value. The operator instructions are at the bottom of the display. "Press (up arrow, down arrow) to change OK when done". If the operator wants to increase the value of the Low Flow Alarm, if the default were lower than 100%, then the up arrow, legend label 220 corresponding to switch "5" 208 can be pressed by the operator and the alarm value in percent will be increased accordingly and displayed on display 198. Similarly, by pressing switch "6" 210 which corresponds to label legend 222 which illustrates the down arrow, the alarm value will decrease and be reflected by the change in the highlighted number on the display 198. Once the operator is satisfied with the alarm threshold, then switch "1" 212 is pushed which corresponds to the legend label "OK" which tells the computer that the selection is complete. The computer stores this new value as the new Alarm Volume value. The value 324 in FIG. 19 will then be updated to the Alarm Volume selection just made by the operator.

FIG. 18 again illustrates the "System" display. The "Battery" function has been described. To activate the "Status" display as indicated by label legend 216, then switch "3" 204 would be pushed. This action would yield FIG. 24.

Figure 23:
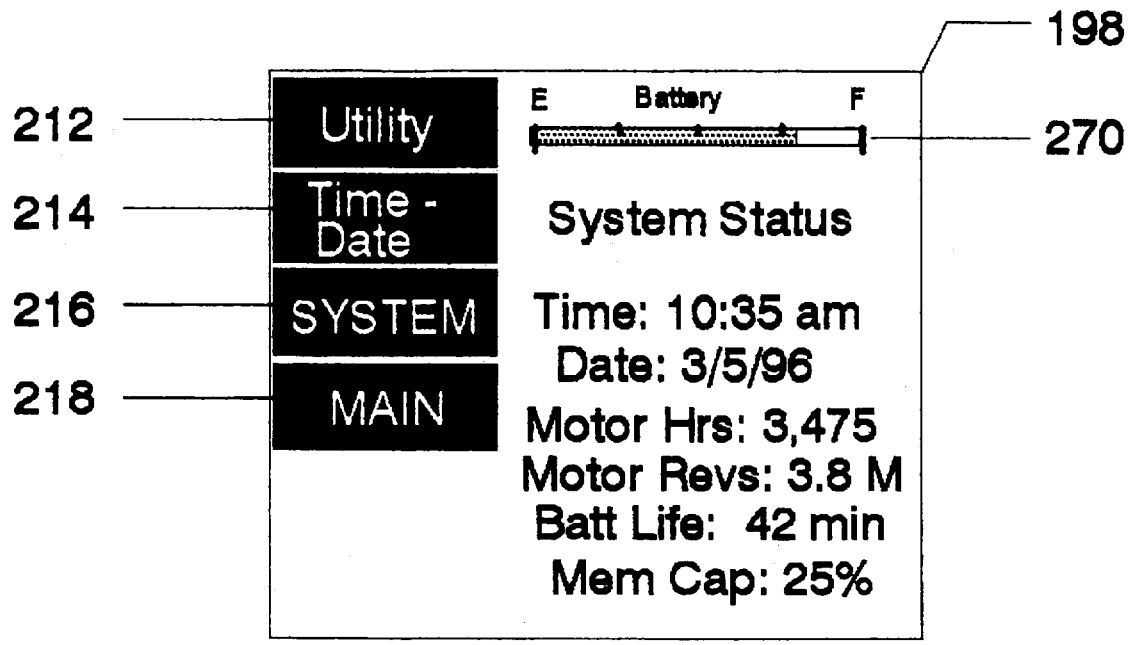
FIG. 23. is a view of the Status Screen of the LCD on the operations panel of the centrifugal pump driver.

FIG. 23 is the System Status display 198. Below the battery indicator 270 is the header 37 System Status" and then the status information. The first status line is the current time which is shown to be 10:35 am and is updated from a real time clock in the console 121. The second Is status line is the current time, which is shown to be Mar. 5, 1996 and is also updated from a real time clock in the console 121. The third line is the number of hours that the motor 108 has cumulatively operated. This value comes from monitoring the hours that the pump has operated and updating the memory on circuit board 112. This value is downloaded to a circuit 148 in the console 121 and updated by the microprocessor on circuit board 148. This value is updated on a periodic basis and copied to the memory on circuit board 112. The third status line is the number of motor revolutions in millions of cycles. This is a calculated value by the microprocessor on circuit board 148 and updated to the memory on circuit board 112 in a similar fashion to the motor hours values just described. The battery life is the next status value and is calculated from the current status of the batteries and mathematically predicted. The last status line is the memory capacity. This memory is shown to be approximately 75% full or 25% empty. This feature will be subsequently described. The label legends indicate "Utility" 212, "Time-Date" 214, "System" 216, and "Main" 218. Pressing switch "1" 200 activates the "Utility" display which is reflected in FIG. 24.

Figure 24:
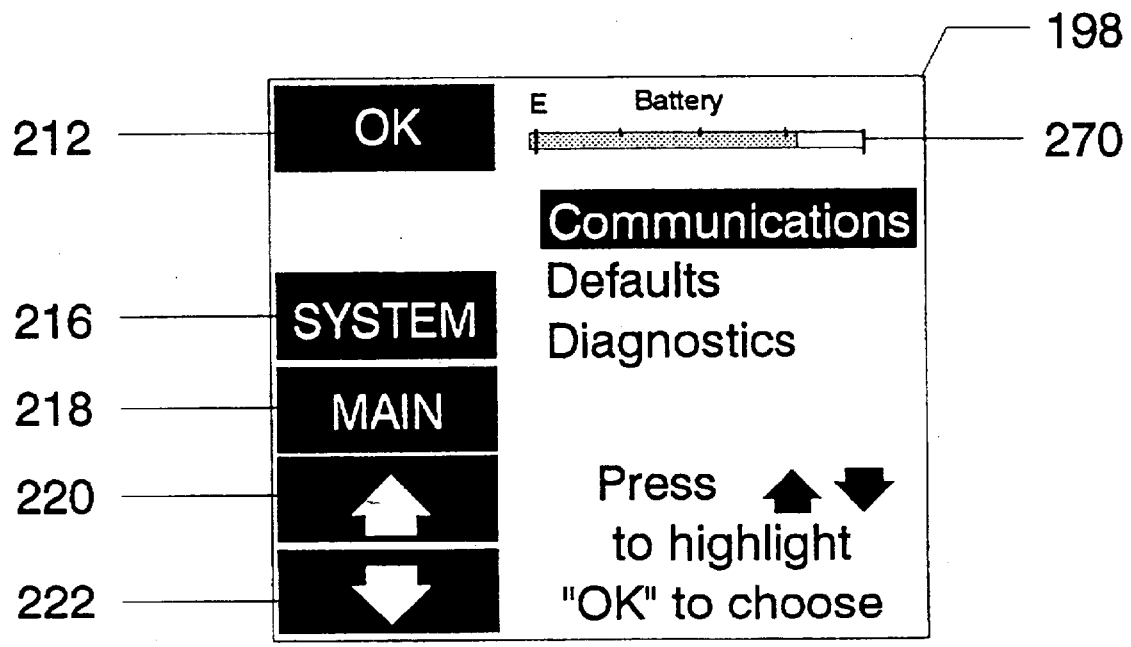
FIG. 24. is a view of the Utility Screen of the LCD on the operations panel of the centrifugal pump driver.

FIG. 24 illustrates the Utility menu and the label legends "OK" 212, "System" 216, "Main" 218, Up Arrow 220 and Down Arrow 222. Below the battery indicator 270 are three immediate lines: "Communications" which is highlighted, "Defaults" and "Diagnostics". Below these are the instructions "Press (up arrow, down arrow) to highlight "OK" to choose" As in previous menus the up arrow 220 is activated by pushing switch "5" 208 and the down arrow 222 is activated by pushing switch "6" 210. This action scrolls the highlighted display between "Communications", "Defaults" and "Diagnostics". Pressing "OK" switch "1" 200 to activate the "OK" label legend 212 transfers the display to the highlighted menu. Pressing switch "1" 200 with the highlighted menu indicating "Communications" will bring up the display 198 indicated by FIG. 25.

Figure 25:
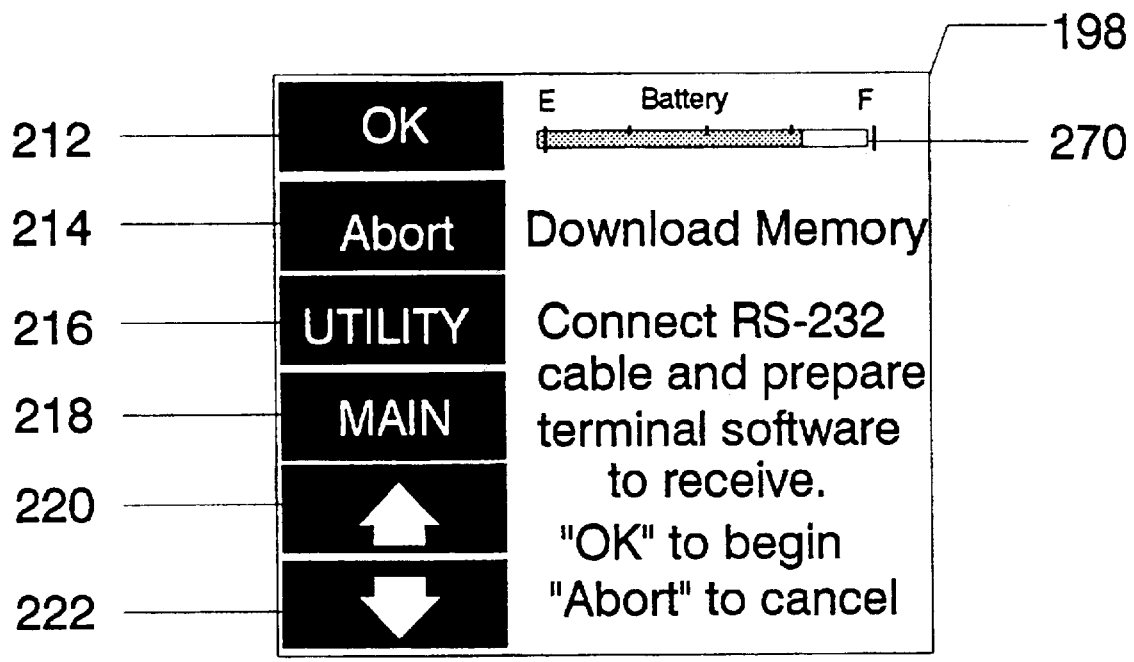
FIG. 25. is a view of the Communications Screen of the LCD on the operations panel of the centrifugal pump driver.

FIG. 25 is the Communications screen on display 198. The display carries instructional information below the battery indicator 270. The intent of this menu is to allow an external cable to another computer to be connected to connector 128 (FIG. 1). FIG. 25 instructs the operator to establish this connection, prepare the other computer to receive information and to press switch "1" 200 corresponding to label 212 which carries the legend "OK" to initiate the computer communication process. If switch "2" 202 is pushed corresponding to label 214 which carries the legend "Abort" then the menu returns to that indicated by FIG. 24. Once the communications link has been established and the console 100 has downloaded its information, the display returns to that as indicated by FIG. 24.

Figure 26:
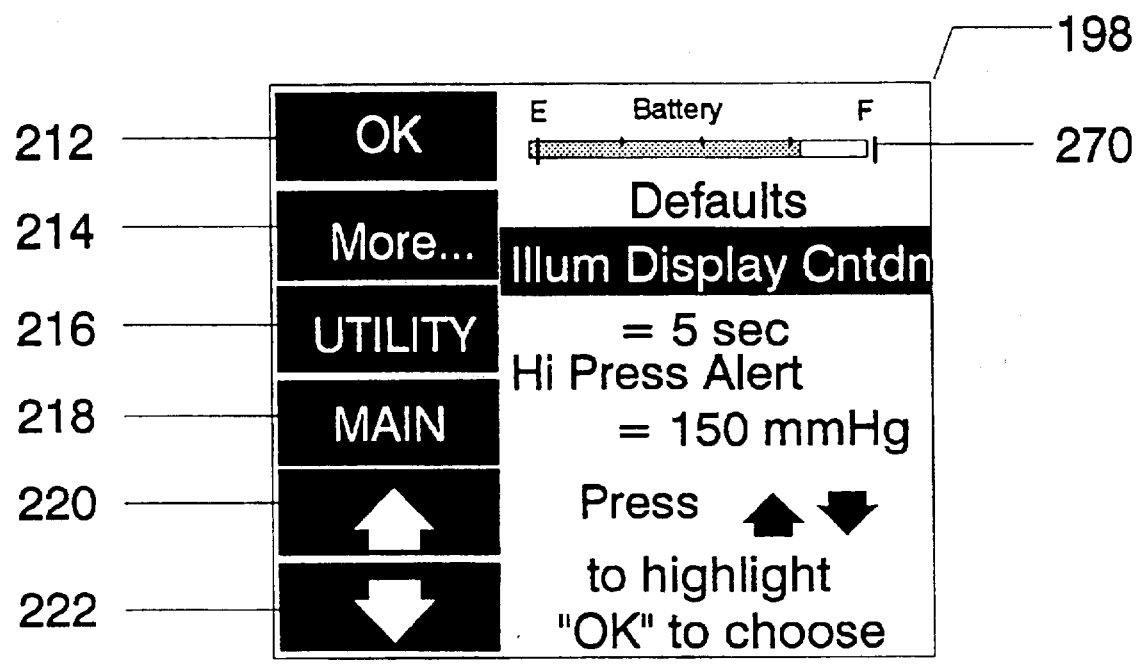
FIG. 26. is a view of the Defaults Screen of the LCD on the operations panel of the centrifugal pump driver with Illuminate Display Countdown highlighted.

FIG. 26 illustrates the Defaults display as scrolled and selected from FIG. 24 using the up and down arrow and the "OK" option as previously described. Below the battery indication 270 on this display 198 is the "Defaults" header and below that is a highlighted "Ilium Display Cntdn" or Illuminate Display Countdown. In this instance the next line illustrates that the display countdown is 5 seconds which is highlighted. The next default is shown as the High Pressure Alert and its default value of 150 mmHg. As in prior menus the up and down arrows are used to highlight the menu of interest and "OK" is activated by pressing switch "1" 200 which activates the selected menu. In this case FIG. 27 illustrates the "Ilium Display Cntdn" menu.

Figure 27:
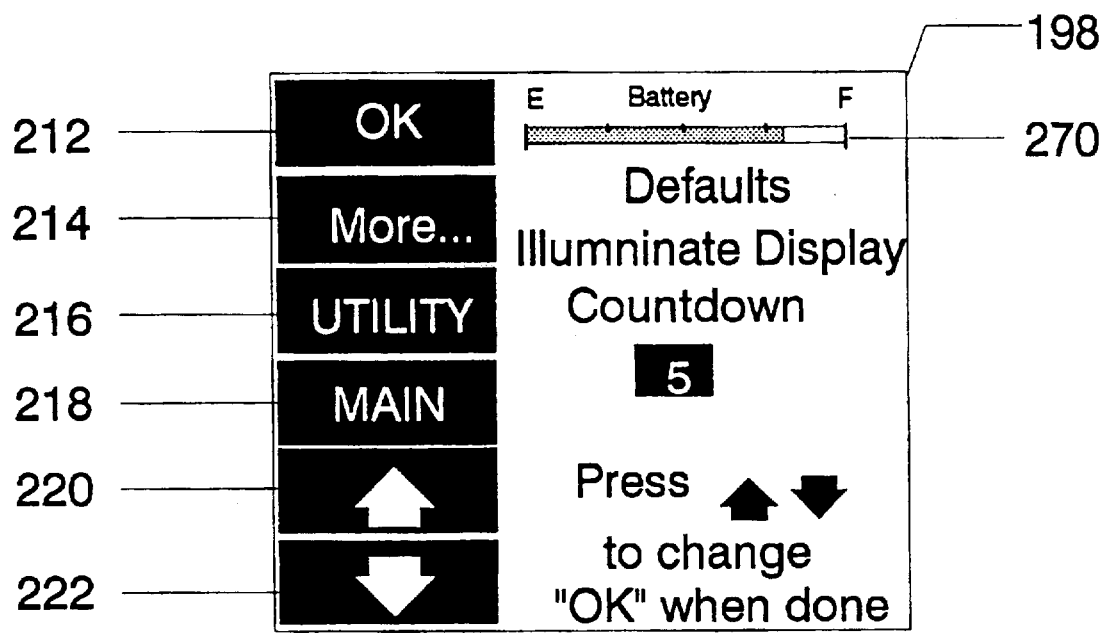
FIG. 27. is a view of the Illuminate Display Countdown Default Screen of the LCD on the operations panel of the centrifugal pump driver.

FIG. 27 shows the Illuminate Display Countdown menu as shown below the battery indicator 270. The default value is shown as 5 seconds and is shown highlighted. As in prior menus, the up and down arrows are used to increase or decrease this value. In this case the default values are increased or decreased in one second increments. Once the operator is satisfied with the result then "OK" is pushed and the computer memory stores this value as the new default and returns the operator to FIG. 26.

Figure 28:
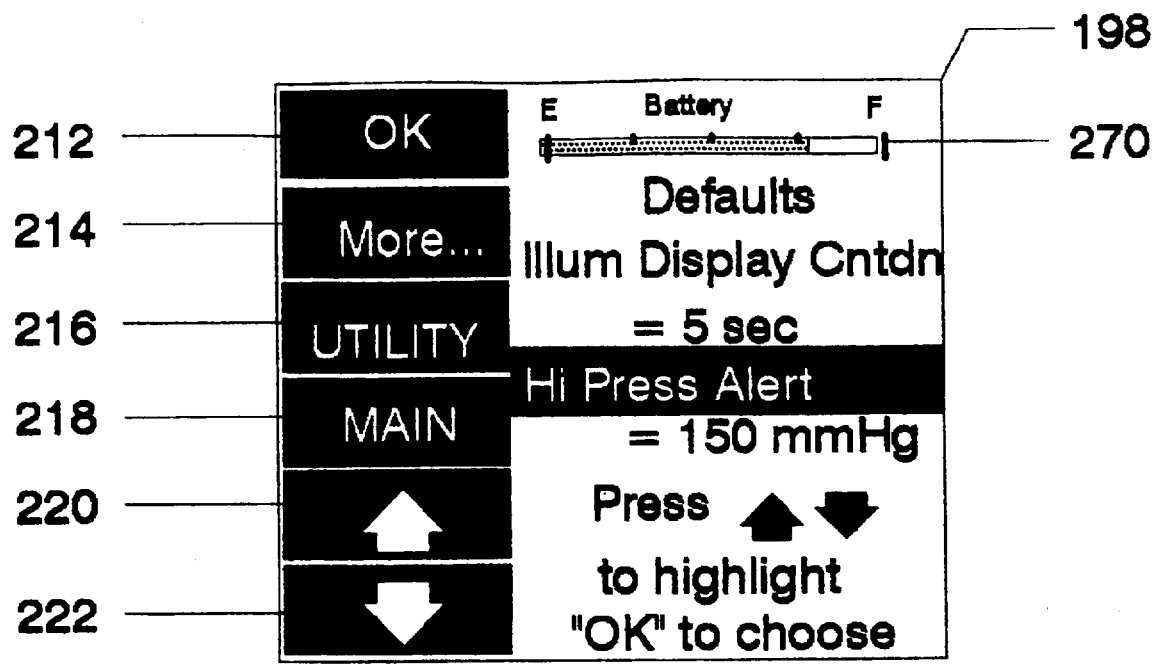
FIG. 28. is a view of the Defaults Screen of the LCD on the operations panel of the centrifugal pump driver with Hi Pressure Alert highlighted.

In FIG. 26, if the up and down arrows are used to highlight "Hi Pressure Alert" then the display changes to represent FIG. 28.

Figure 29:
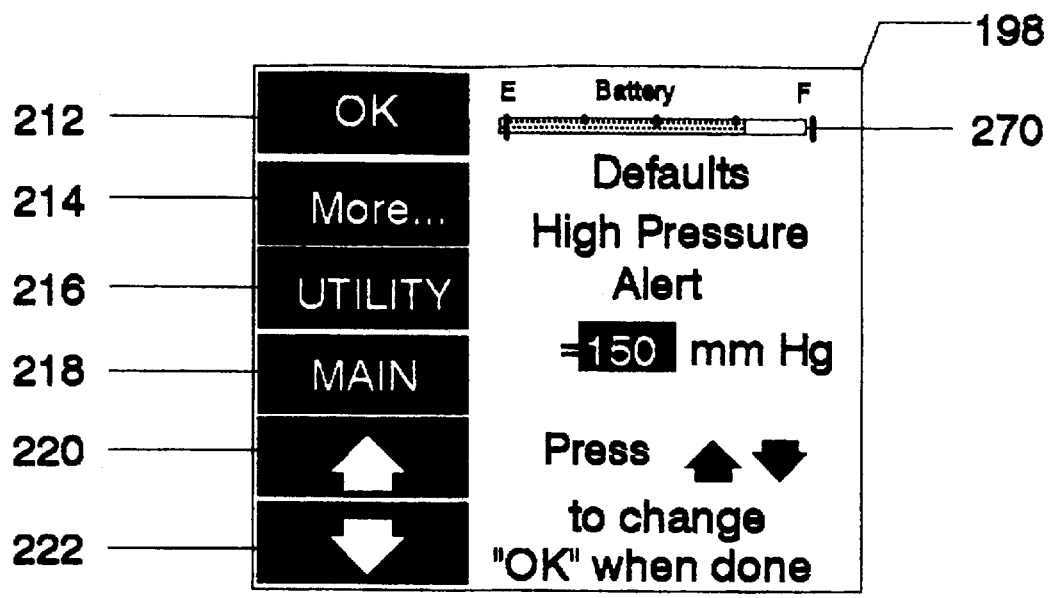
FIG. 29. is a view of the High Pressure Alert Default Screen of the LCD on the operations panel of the centrifugal pump driver.

In FIG. 28 if the "OK" is activated via pushing switch "1" 200 which corresponds to label 212 containing the legend "OK" then the screen changes to that represented by FIG. 29.

FIG. 29 is the High Pressure Alert Default Screen which carries this header below the battery indicator 270. The value of this default is highlighted as 150 mmHg. As before, the operator uses the up and down arrows to increase or decrease this value in increments of 5 mmHg and then presses switch "1" 200 which corresponds to label 212 containing the legend "OK" to change the default to the one selected. The screen then changes back to the one indicated in FIG. 28.

In FIG. 28 label 214 carries the legend "More . . .". If this is chosen by pressing switch "2" 202 then FIG. 30 is shown on the display 198.

The FIG. 30 display 198 also has two defaults shown below the battery indicator 270. These defaults are "Low Flow Alarm" which is shown highlighted, whose default value is 1.0 LPM and "Neg. Flow Alarm" which is shown below this and carries an illustrated default value of 0.3 LPM. Selecting "OK", label legend 212 corresponding to switch "1" 200 with "Low Flow Alarm" highlighted changes the display to FIG. 31.

Figure 30:
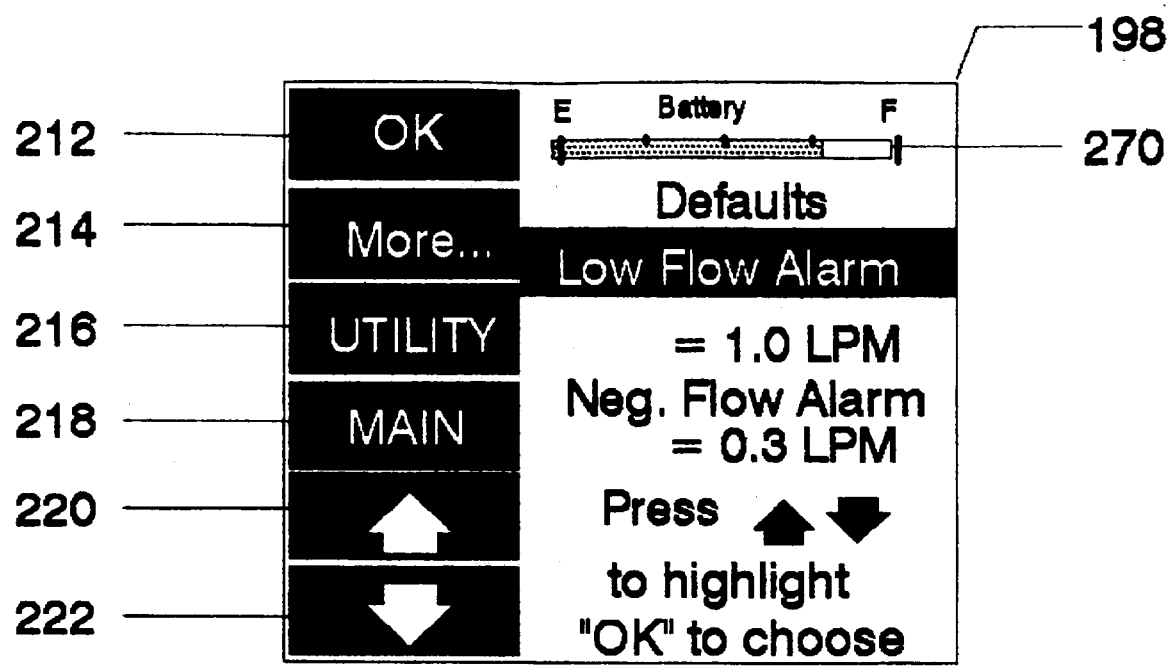
FIG. 30. is a view of the Defaults Screen of the LCD on the operations panel of the centrifugal pump driver with Low Flow Alarm highlighted.
Figure 31:
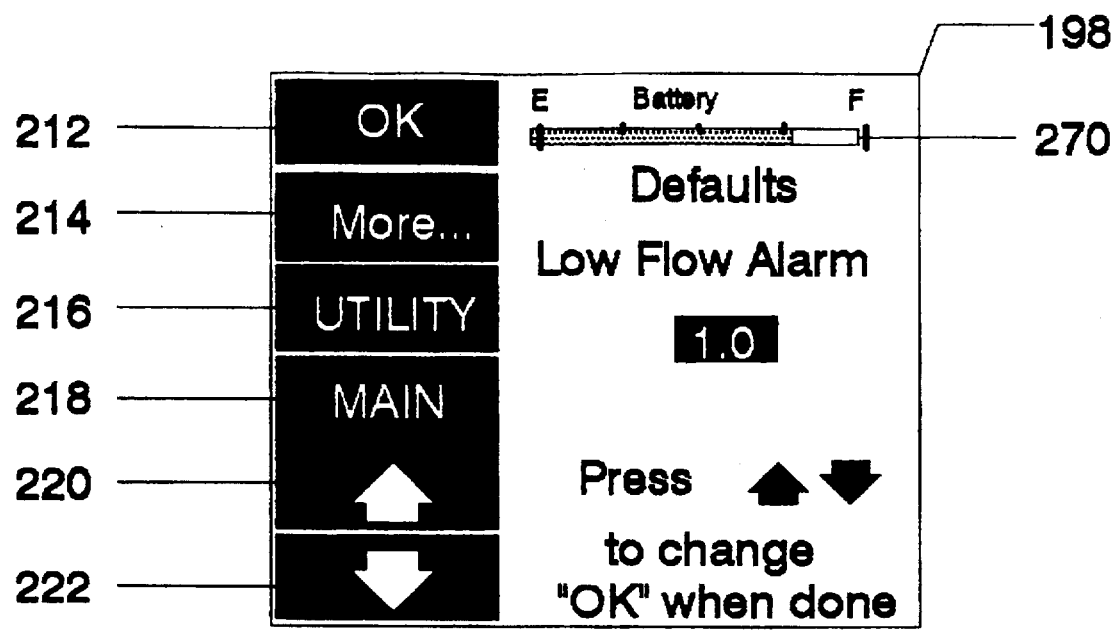
FIG. 31 is a view of the Low Flow Alarm Default Screen of the LCD on the operations panel of the centrifugal pump driver.

FIG. 31 is the Low Flow Alarm Default screen on display 198 which carries this header below the battery indicator 270. The value of this default is highlighted as 1.0 LPM. As before, the operator uses the up and down arrows to increase or decrease this value in increments of 0.1 LPM and then presses switch "1" 200 which corresponds to label 212 containing the legend "OK" to change the default to the one selected. The screen then changes to the one indicated in FIG. 30.

Figure 32:
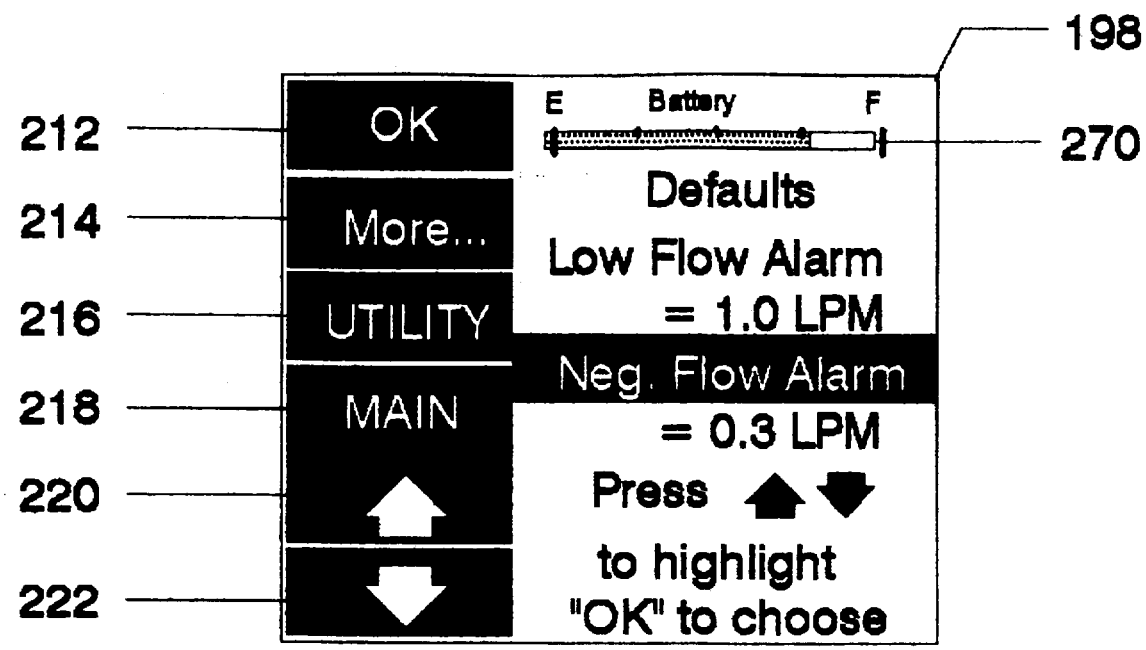
FIG. 32. is a view of the Defaults Screen of the LCD on the operations panel of the centrifugal pump driver with Neg Flow Alarm highlighted.

If, in FIG. 30 the highlight is scrolled from "Low Flow Alarm" to "Neg Flow Alarm" using the down arrow then the result is FIG. 32.

As stated, FIG. 32 is principally FIG. 30 with "Neg Flow Alarm" now highlighted. This is accomplished by using the up and down arrows to move the highlighting to "Neg Flow Alarm" and selecting "OK", label legend 212 corresponding to switch "1" 200. Upon activating the "Low Flow Alarm" option the display changes to FIG. 33.

Figure 33:
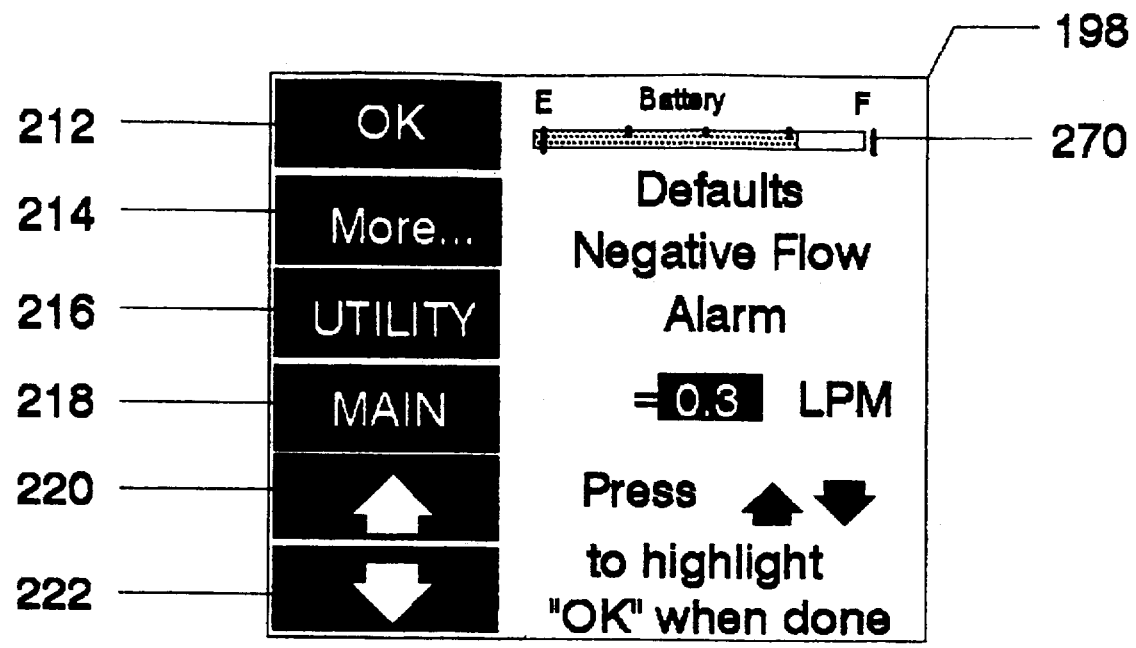
FIG. 33. is a view of the Negative Flow Alarm Default Screen of the LCD on the operations panel of the centrifugal pump driver.

FIG. 33 is the Neg Flow Alarm Default screen on display 198 which carries this header below the battery indicator 270. The value of this default is highlighted as 0.3 LPM. As before, the operator uses the up and down arrows to increase or decrease this value in increments of 0.1 LPM and then presses switch "1" 200 which corresponds to label 212 containing the legend "OK" to change the default to the one selected. The screen then changes back to the one indicated in FIG. 32.

Figure 34:
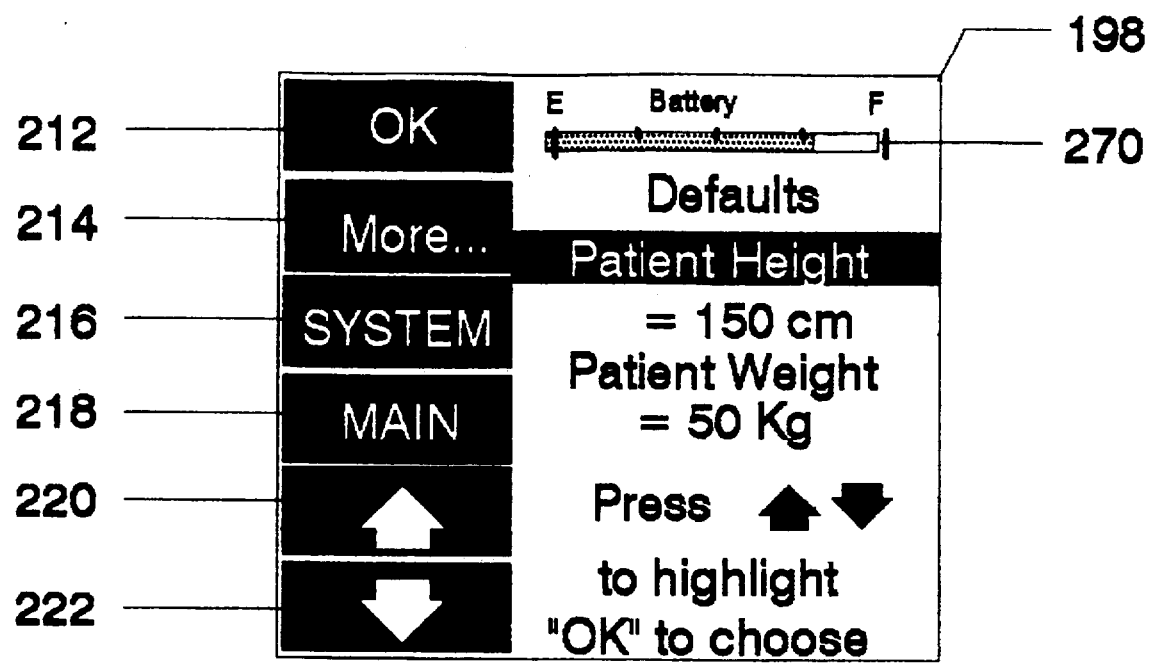
FIG. 34 is a view of the Defaults Screen of the LCD on the operations panel of the centrifugal pump driver with Patient Height highlighted.

In FIG. 30, if the operator, selects "More . . .", label legend 214 by pressing switch "2" 202 then the display 198 will change to FIG. 34.

FIG. 34 is the Patient Height and Patient Weight Default menu as stated below the battery indicator 270. As in previous menus the up and down arrows can be used to highlight either the Patient Height or the Patient Weight. Activating the "OK" by highlighting the Patient Height using methods previously described will transfer the display to FIG. 35.

Figure 35:
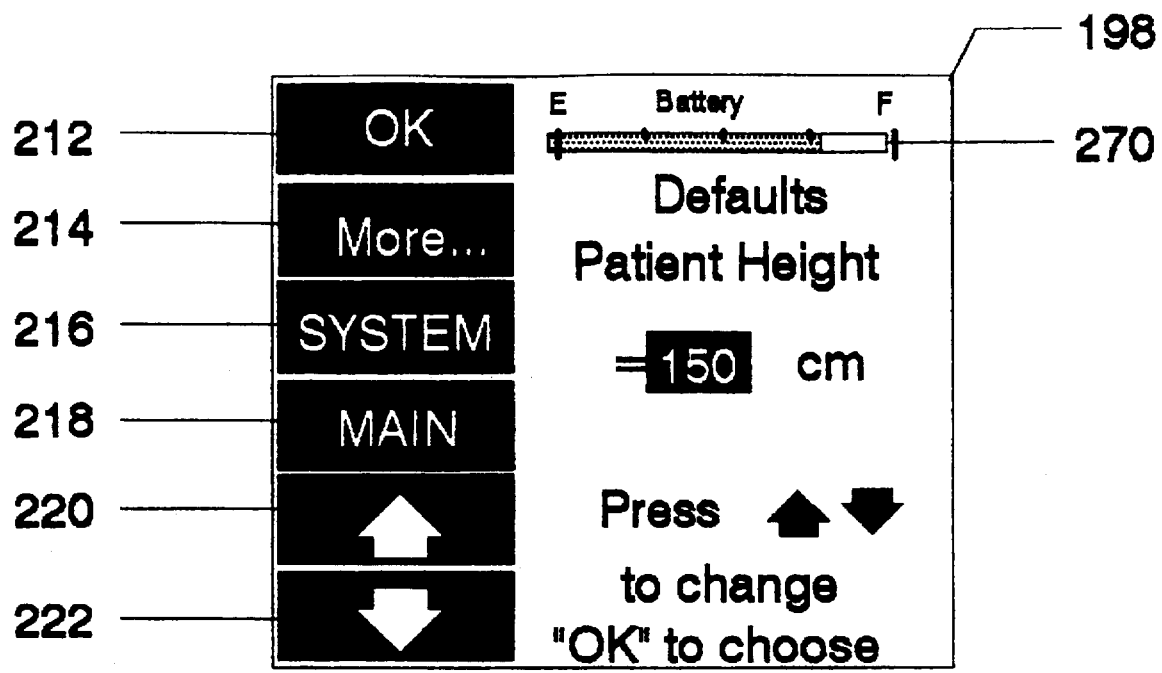
FIG. 35. is a view of the Patient Height Default Screen of the LCD on the operations panel of the centrifugal pump driver.

FIG. 35 is the display used to change the default for Patient Height. The value of this default is highlighted as 150 cm. As before, the operator uses the up and down arrows to increase or decrease this value in increments of 2 cm and then presses switch "1" 200 which corresponds to label 212 containing the legend "OK" to change the default to the one selected. The screen then changes back to the one indicated in FIG. 34.

Figure 36:
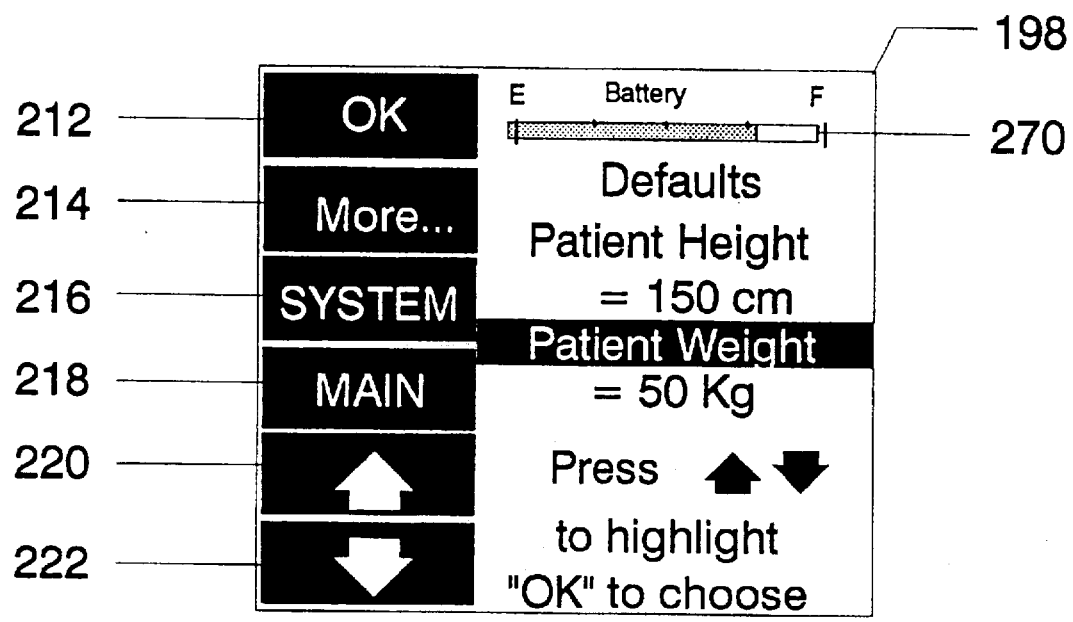
FIG. 36. is a view of the Defaults Screen of the LCD on the operations panel of the centrifugal pump driver with Patient Weight highlighted.

FIG. 36 is the same display as FIG. 33 except that Patient Weight is now highlighted. Activating the "OK" with the Patient Height highlighted using methods previously described will transfer the display to FIG. 37.

Figure 37:
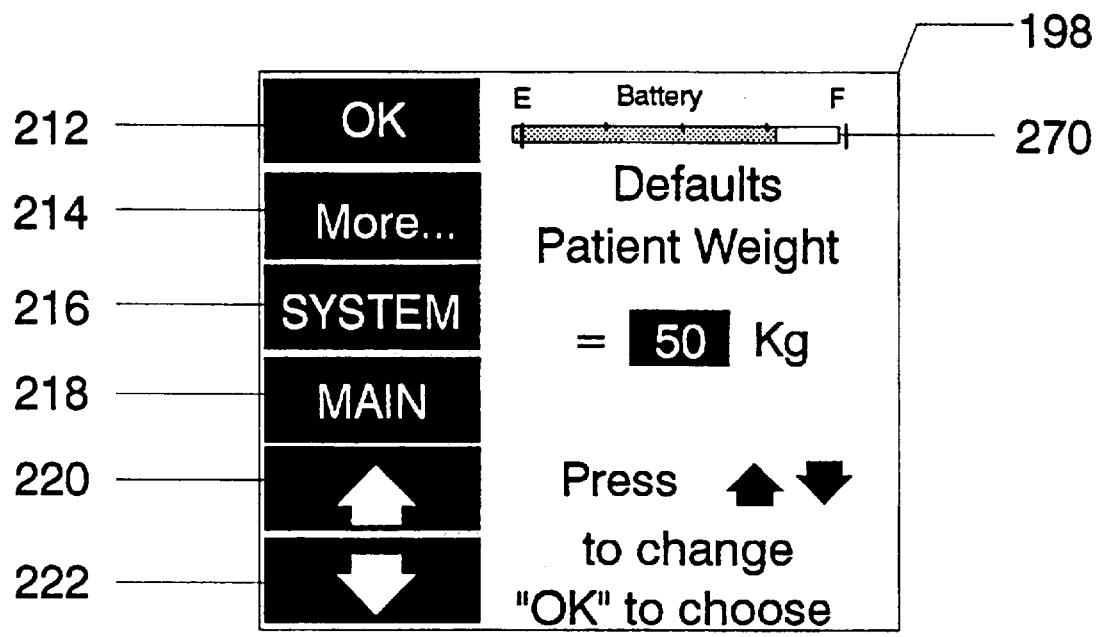
FIG. 37. is a view of the Patient Weight Default Screen of the LCD on the operations panel of the centrifugal pump driver.

FIG. 37 is the display used to change the default for Patient Weight. The value of this default is highlighted as 50 Kg. As before, the operator uses the up and down arrows to increase or decrease this value in increments of 1 Kg and then presses switch "1" 200 which corresponds to label 212 containing the legend "OK" to change the default to the one selected. The screen then changes back to the one indicated in FIG. 36.

Figure 38:
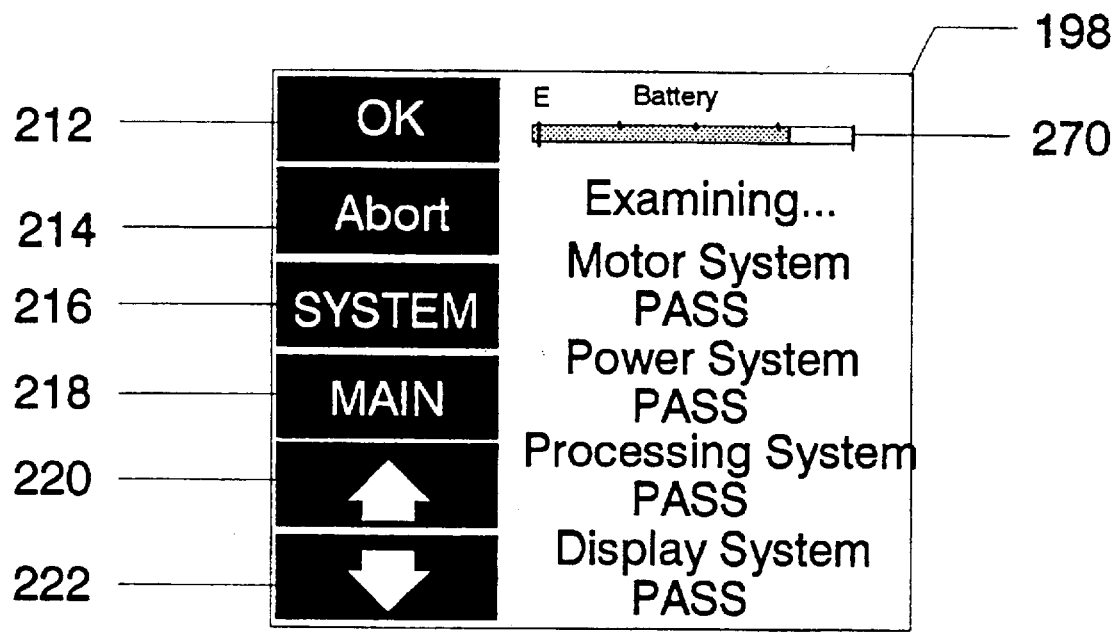
FIG. 38. is a view of the Diagnostics Screen of the LCD on the operations panel of the centrifugal pump driver.

Returning to FIG. 24, if the down arrow is used to highlight "Diagnostics" and activating "OK" by methods previously described, FIG. 38 is the result.

In the display 198 of FIG. 38 the system will self check all of the internal systems and report any found anomalies on the display 198. This display is also useful for service technicians who may wish to use advanced status checks for determining the condition of the system 100.

Figure 39:
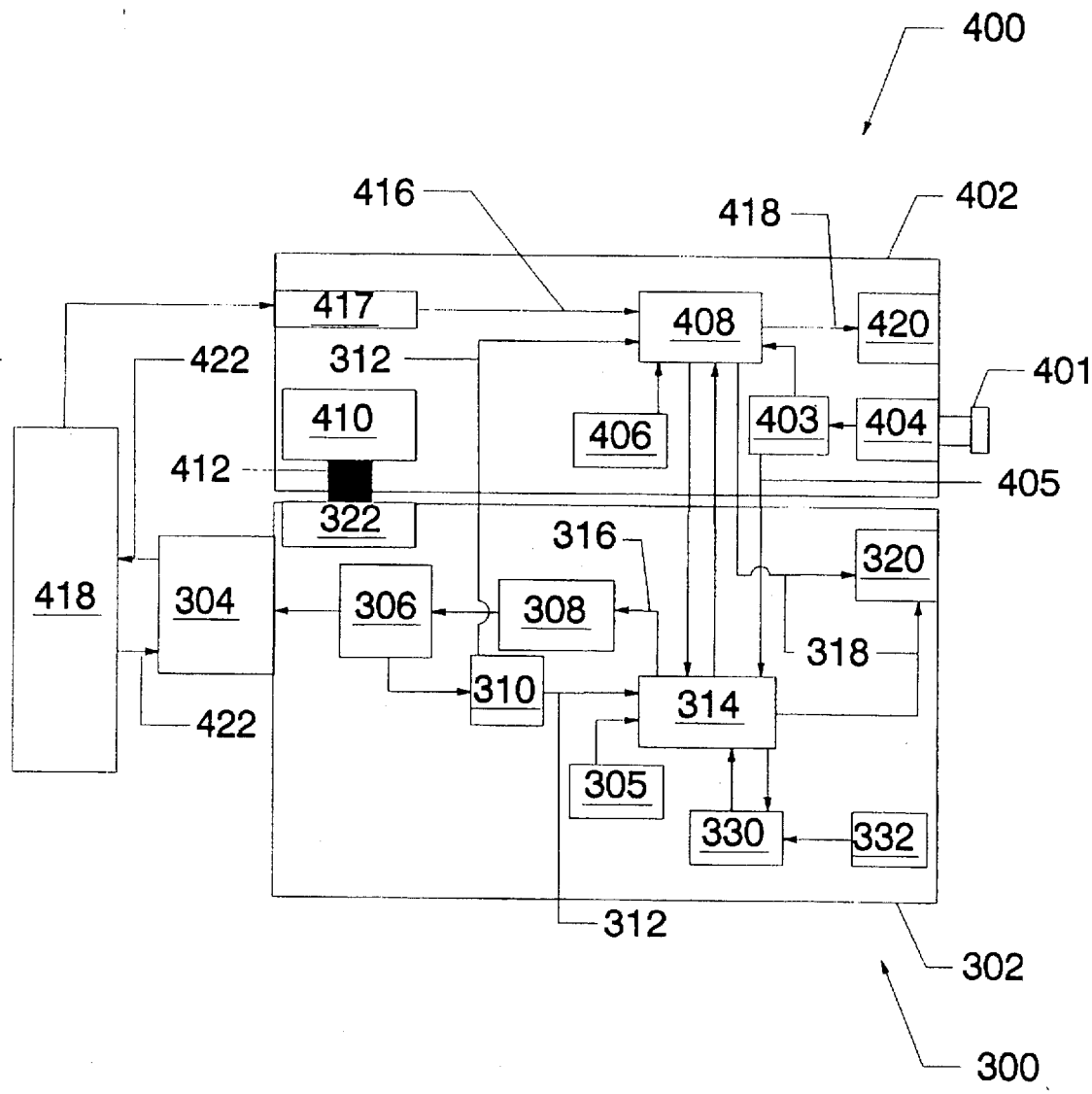
FIG. 39 is a block diagram of an embodiment of the invention.

Referring to FIG. 39, the foregoing embodiments in FIGS. 1–38 are illustrated in block diagram. From this diagram and the foregoing description of the preferred embodiment, it will now be appreciated that a centrifugal pump motor system 300 and console system 400 have been described which comprise a motor housing 302, motive means in motor housing 302 adapted to connect to a centrifugal pump 304 to rotationally drive the centrifugal blood pump, the motive means including a motor 306 for rotationally driving centrifugal blood pump 304 and a controller 308 operatively associated with motor 306 for controlling the rotational speed of motor 306. Sensors 310 are operatively associated with motor 306 for sensing the motor rotational speed and outputting a monitor signal 312 signifying the rotational speed. A console 402 separate from motor housing 302 includes a speed selector 404. Speed selector 404 in console 402 includes a potentiometer 401 for producing an analog speed signal and analog to digital converter 403 for converting the analog signal to a digital speed signal for generating a selected speed signal 405 The selected speed signal 405 signifies a selected rotational speed for motor 306. Motor housing microprocessor 314 in motor housing 302 is in electrical connection with motor housing program memory 305, controller 308, and speed selector 404 via analog to digital converter 403, under program control of 305, receives selected speed signal 405 and generates a speed control signal 316 to controller 308 signifying the selected speed for controller 308.

Console microprocessor 408 in console 402 is in electrical connection with console program memory 406, speed selector 404 via analog to digital converter 403, speed sensors 310, and motor housing microprocessor 314, under program control of program memory 406, for receiving speed signal 405 and monitor signal 312 and determining whether monitor signal 312 is within a predetermined limit of allowable variance of the speed signal, and if within the allowable limit, then outputting display signal 318 and 418, but if outside the allowable limit under a predetermined sampling protocol, then outputting an alarm signal (also indicated by 318 and 418). A display 320 in motor housing 302 and display 420 in console 402 is in electrical communication with console microprocessor 408 and is responsive to display signal 318 and 418 for displaying information. Source power 410 in the console supplies a source of DC power. Circuitry in motor housing 302 and in console 402 (the circuitry is indicated generally by the lines connecting the block components) and electrically conductive cable 412 interconnect the console circuitry for transmission of DC power to the motor housing circuitry 322 from the console power source 410 and to provide electrical communication between all electrical components, including the speed selector 404, program memory 406 and console microprocessor 408, and motor housing microprocessor 314, controller 308, sensors 310, and display 320.

Volatile memory 330 is included in motor housing 302, as is a DC battery 332 to provide power to motor housing volatile memory 330 when power from the console is absent. The console microprocessor 408 under program control includes means for initially recording identification of the motor and for cumulatively recording motor revolutions, and for saving the identification and the cumulative revolutions to the motor housing battery backed volatile memory 330 while power is supplied to the motor housing circuitry by the external source, and means for reading the identification and cumulative revolutions from the motor housing memory 330 after power is initially supplied to the motor housing circuitry.

The circuitry in the console includes input connectors for receiving one or more input signals 416 from one or more peripheral signaling sources 417 adapted to sense a parameter of a patient 419 connected in a blood flow circuit having an extracorporeal flow portion 422 including centrifugal blood pump 304, or a parameter of the extracorporeal portion of the circuit, or both.

Figure 40:
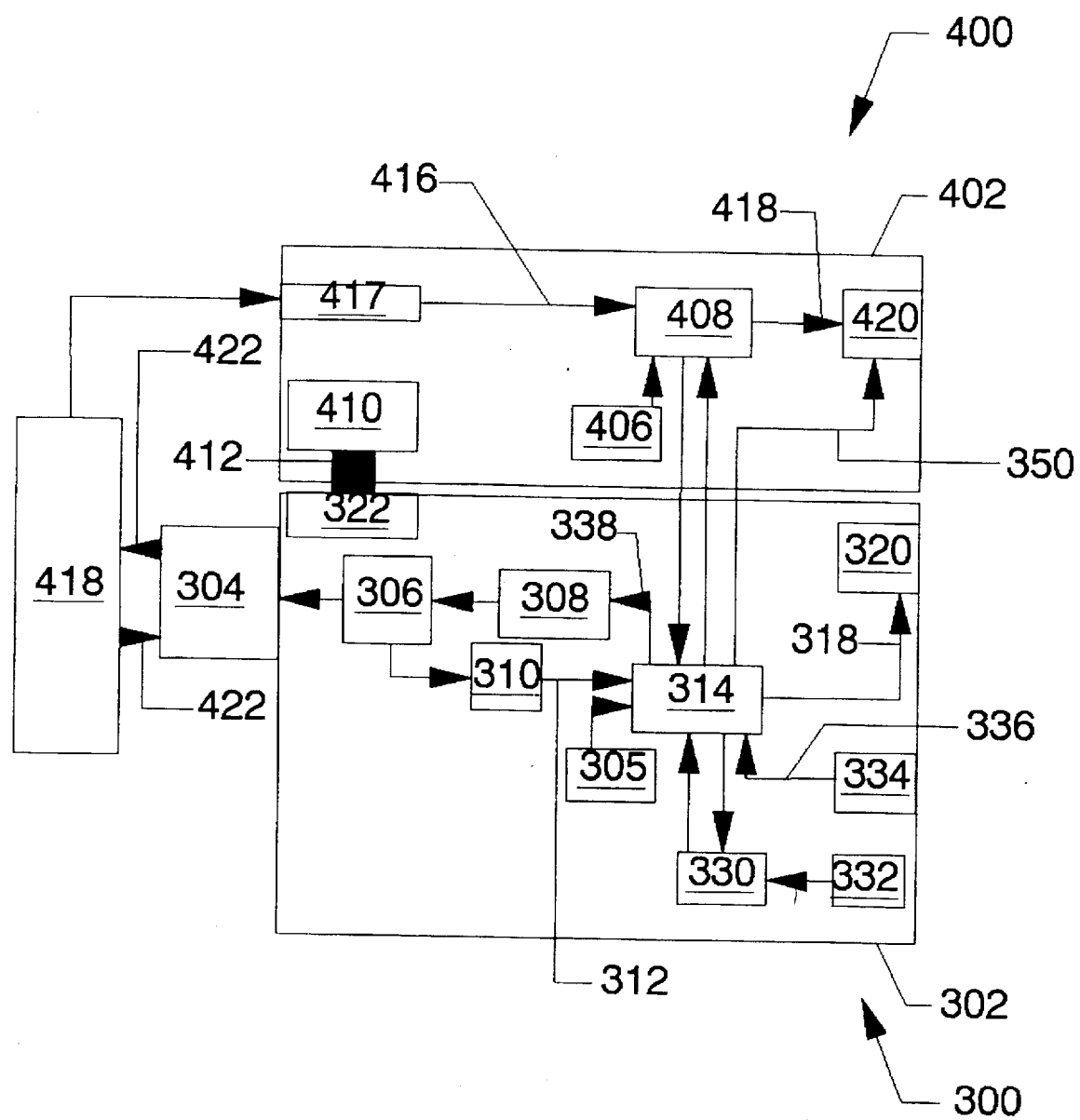
FIG. 40 is a block diagram of another embodiment of the invention.

The more basic configuration of the invention is shown by block diagram in FIG. 40, and comprises a motor housing 302 that contains motive means adapted to connect to a centrifugal pump 304 to rotationally drive the centrifugal blood pump, the motive means including a motor 306 for rotationally driving centrifugal blood pump 304 and a controller 308 operatively associated with motor 306 for controlling the rotational speed of motor 306. Speed selector 334 comprises a set of decrease/increase push digital switches (right double arrow for units of ten increase, right single arrow for single unit increase; left double arrow for units of ten decrease, left single arrow for single unit decrease) for generating a selected speed signal 336 signifying a selected rotational speed for motor 306. Sensors 310 are operatively associated with motor 306 (or controller 308) for sensing the rotational speed of the motive means and outputting a monitor signal 312 signifying the rotational speed. Program memory 305 is contained in motor housing 302 for storage of a program of microprocessor readable instructions. Motor housing microprocessor 314, in electrical connection with controller 308, speed selector 334, sensors 310 and the program memory 305, under program control of program memory 305, receives selected speed signal 336 and generates a speed control signal 338 to controller 308, signifying the selected speed for the controller, and receives monitor signal 312 and outputs display signals 318 and 350. A motor housing display 320 and console display 420 are in electrical communication with microprocessor 314 and are responsive to display signals 318 and 350 for displaying information. Motor housing circuitry provides electrical communication between all electrical components including controller 308, speed selector 334, sensors 310, program memory 305, microprocessor 314, and displays 320 and 420, and electrically conductive cable 412 connected to the motor housing circuitry transmits electrical DC power to the motor housing circuitry from console power source 410.

Having now described our invention the scope of our invention should be understood not limited to the specific preferred embodiments described, but fully as defined in the appended claims.

We claim:

1. An intelligent motor driver apparatus for a centrifugal blood pump, which apparatus comprises:

a motor housing separate from a perfusionist console for monitoring one or more blood flow perfusion parameters in an extracorporeal blood flow circuit that includes a centrifugal blood pump, said housing containing:

motive means adapted to connect to said centrifugal pump to rotationally drive the centrifugal blood pump, said motive means including a motor for rotationally driving the centrifugal blood pump and a controller operatively associated with said motor for controlling the rotational speed of said motor, speed selector means for generating a selected speed signal signifying a selected rotational speed for said motor, sensor means operatively associated with said motive means for sensing the rotational speed of the motive means and outputting a monitor signal signifying such rotational speed, programmable memory programmed with a program of microprocessor readable instructions for microprocessor operations including receiving said selected speed signal and generating a speed control signal to the controller signifying the selected speed for the controller; and receiving said monitor signal and outputting a display signal indicative of motor rotational speed, microprocessor under program control, in electrical connection with said controller, said speed selector means, said sensor means and said program memory, for executing said instructions from said programmed memory to receive said selected speed signal and generate a speed control signal to the controller signifying the selected speed for the controller, and to receive said monitor signal and output a display signal, display means in electrical communication with said microprocessor means and responsive to said display signal for displaying information, motor housing circuitry means for providing electrical communication among said controller, said speed selector means, said sensor means, said program memory, said microprocessor, and said display means, and electrically conductive cable means connected to said motor housing circuitry means for transmitting electrical DC power to said motor housing circuitry means from an external power source.

2. The apparatus of claim 1 wherein said program of microprocessor readable instructions further includes instruction means for microprocessor operations requiring said speed selector means to be set to zero before said motor can be rotated.

3. The apparatus of claim 1 in which said program of microprocessor readable instructions further includes instruction means for microprocessor operations for inputting a minimum speed at which said microprocessor means under program control will ignore a said selected speed signal lower than said minimum speed and generate an alert signal that the said selected speed is lower than the minimum speed.

4. The apparatus of claim 3 further comprising means controllable by an operator and in which said program of microprocessor readable instructions further includes instruction means for microprocessor operations executable by said microprocessor, after said alert signal is generated, for permitting the microprocessor under program control to produce the control signal at said selected speed signal lower than said minimum speed until motor speed is reset above said minimum speed or electrical power to said motor housing circuitry is discontinued.

5. The apparatus of claim 1 comprising means for electronically recording data and in which said microprocessor readable instructions include instructions for writing identification of said motor to said data recording means and/or writing motor use history to said data recording means while power is supplied to said motor housing circuitry, and reading said identification and/or motor use history from said data recording means when power is initially supplied to said motor housing circuitry, and generating signals representing said motor identification and/or motor use history, and wherein said display means are responsive to signals from said microprocessor on microprocessor execution of said reading and signal generation instructions, for displaying motor identification and/or motor use history.

6. A centrifugal blood pump control system comprising:
a perfusionist console for monitoring one or more blood flow perfusion parameters in an extracorporeal blood flow circuit that includes a centrifugal blood pump,
an intelligent motor driver apparatus separate from said console which comprises:
a motor housing;
motive means in said motor housing adapted to connect to a centrifugal pump to rotationally drive the centrifugal blood pump, said motive means including a motor for rotationally driving the centrifugal blood pump and a controller operatively associated with said motor for controlling the rotational speed of said motor,
sensor means in said motor housing operatively associated with said motive means for sensing the rotational speed of the motive means and outputting a monitor signal signifying such rotational speed,
speed selector means in one of said console or said motor housing for generating a selected speed signal signifying a selected rotational speed for said motor,
means in said motor housing for electronically recording data,
programmable memory in said motor housing programmed with a program of microprocessor readable instructions, for microprocessor operations including, receiving said selected speed signal, and generating a speed control signal to the controller signifying the selected speed for the controller, receiving said monitor signal, and outputting a display signal indicative of motor rotational speed, writing identification of said motor to said data recording means and/or writing motor use history to said data recording means while power is supplied to said motor housing circuitry, and reading said identification and/or motor use history from said data recording means when power is initially supplied to said motor housing circuitry, and generating signals representing said motor identification and/or motor use history, microprocessor in said motor housing under program control, in electrical connection with said program memory, said controller, and said speed selector means, for executing said instructions, to receive said selected speed signal and generate a speed control signal to the controller signifying the selected speed for the controller, and to write identification of said motor to said data recording means and/or write motor use history to said data recording means while power is supplied to said motor housing circuitry, and to read said identification and/or motor use history from said data recording means when power is initially supplied to said motor housing circuitry, and to generate signals representing said motor identification and/ or motor use history, display means in said motor housing in electrical communication with said motor housing microprocessor and responsive to said display signal for displaying information and to said signals representing motor identification and/or motor use history for displaying motor identification and/or motor use history, motor housing circuitry means in said motor housing for providing electrical communication among at least said controller, said sensor means, said program memory, said microprocessor, and said display means, console power means in said console for supplying a source of DC power, and console circuitry means in said console and electrically conductive cable tethering means for electrically interconnecting said console circuitry means and said motor housing circuitry means and for transmission of DC power to said motor housing circuitry means from said console power means.

7. The apparatus of claim 6 in which said console circuitry means further comprises:

means adapted to receive one or more input signals from one or more peripheral signaling sources adapted to sense one or more parameters of a patient connected in a blood flow circuit having an extracorporeal flow portion including a centrifugal blood pump, or a parameter of the extracorporeal portion of said circuit, or both, and wherein said console further comprises console display means for displaying information.

8. The apparatus of claim 7 in which
said console circuitry means further comprises a console microprocessor and condole program memory for storage of a program of microprocessor readable instructions for said console microprocessor, and
said console microprocessor is responsive to program instructions from said console program memory to interpret said input signals from said one or more peripheral signaling sources into information values and output signals to said console display means to display said input based information values.

9. The apparatus of claim 8 in which said console display means includes a light screen responsive to said console microprocessor under program control to display screen images including information and menu options for calling different screens.

10. The apparatus of claim 9 in which said screen comprises a liquid crystal display screen.

11. The apparatus of claim 8 in which said console display means includes a scalar display of a predetermined original range of values and high limit that is automatically convertible a predetermined number of times by said console microprocessor under program control to a predetermined different range of values and high limit when the next previous high limit is reached.

12. The display of claim 11 in which said scaler display comprises an array of light emitting diodes and associated drivers.

13. The apparatus of claim 7 in which said console includes:
a power cord for receiving AC power, and
power supply means electrically connected to said console circuitry and said power cord for converting AC line voltage to DC voltage.

14. The apparatus of claim 13 in which
said power means in said console includes at least one on-board DC battery and a connector for an external DC power source both connected to said console circuitry, and in which said console further includes a console microprocessor and console program memory for storage of a program of microprocessor readable instructions for said console microprocessor means, and
said console microprocessor under program control is electrically connected by said console circuitry to said console power supply means, said console on-board battery and said console external DC power source connector, and further comprises:
means for determining what power is available from the console power sources comprising said power supply means, said on-board DC battery and said external DC power source connector,
means for prioritizing and distributing power such that if DC power is available from said console power supply means, it has priority, but if DC power is not available from said console power supply means and external DC power from said console external DC power source connector is available, then it has priority, but if both DC power from said console power supply means and from said console external DC power source connector are not available, then said on-board console battery has priority, and
means for trickle charging said on-board console battery when DC power from said console power supply means is available.

15. A centrifugal blood pump control system comprising:
a perfusionist console for monitoring one or more blood flow perfusion parameters in an extracorporeal blood flow circuit that includes a centrifugal blood pump,
an intelligent motor driver apparatus separate from said console, which comprises:
a motor housing,
motive means in said motor housing adapted to connect to a centrifugal pump to rotationally drive the centrifugal blood pump, said motive means including a motor for rotationally driving the centrifugal blood pump and a controller operatively associated with said motor for controlling the rotational speed of said motor,
sensor means in said motor housing operatively associated with said motive means for sensing the rotational speed of the motive means and outputting a monitor signal signifying such rotational speed,
speed selector means in said console for generating a selected speed signal signifying a selected rotational speed for said motor,
motor housing programmable memory in said motor housing programmed with a program of microprocessor readable instructions, for microprocessor operations including,
receiving said selected speed signal, and generating a speed control signal to the controller signifying the selected speed for the controller,
a motor housing microprocessor in said motor housing in electrical connection with said program memory, said controller, and said speed selector means, and under program control of said motor-housing program memory, for executing said instructions, to receive said selected speed signal and generate a speed control signal to the controller signifying the selected speed for the controller,
console programmable memory in said console programmed with a program of microprocessor readable instructions, for microprocessor execution including, for receiving said selected speed signal and said monitor signal,
determining whether the monitor signal is within a predetermined limit of allowable variance of the speed signal, and
if within the allowable limit, then outputting a display signal, but
if outside the allowable limit under a predetermined sampling protocol, then outputting an alarm signal,
a console microprocessor in said console in electrical connection with said console program memory, said speed selector means, said sensor means, and said motor housing microprocessor, and under program control of said console program memory, for execution of said instructions of said programmed memory of said console microprocessor,
display means in said motor housing in electrical communication with said console microprocessor and responsive to said display signal for displaying information,
power means in said console for supplying a source of DC power, and
circuitry means in said motor housing and in said console and electrically conductive cable means interconnecting said circuitry means for transmission of DC power to said motor housing circuitry means from said console power means and for providing electrical communication between said speed selector means, said program memory and said console microprocessor and said motor housing microprocessor, said controller, said sensor means, and said display means.

16. The apparatus of claim 15 in which said speed selector means includes:

potentiometer means for producing an analog speed signal; and analog to digital conversion means for converting said analog speed signal to a digital speed signal.

17. The apparatus of claim 15 wherein said motor housing further contains volatile memory and a DC battery to provide power to said motor housing volatile memory when power from said console is absent, and said console microprocessor under program control further comprises 'means for initially recording identification of said motor and for cumulatively recording motor revolutions, and for saving said identification and the cumulative revolutions to said motor housing battery backed volatile memory while power is supplied to said motor housing circuitry by said external source, and means for reading said identification and cumulative revolutions from said motor housing memory after power is initially supplied to said motor housing circuitry.

18. The apparatus of claim 17 in which said circuitry means of said console further includes:

input means adapted to receive one or more input signals from one or more peripheral signaling sources adapted to sense a parameter of a patient connected in a blood flow circuit having an extracorporeal flow portion including a centrifugal blood pump, or a parameter of the extracorporeal portion of said circuit, or both.

19. The apparatus of claim 18 in which said console microprocessor under program control further includes:

means for interpreting said input signals from said one or more peripheral signaling sources and for outputting display signals to said console display means to display information based on said input signals.

20. The apparatus of claim 19 in which said console housing further contains volatile memory, and said console microprocessor under program control further includes means for writing data to said console volatile memory while power from said external source is present.

21. The apparatus of claim 19 in which said console display means includes a light screen responsive to said console microprocessor under program control to display screen images including information and menu options for calling different screens.

22. The apparatus of claim 21 in which said screen comprises a liquid crystal display screen.

23. The apparatus of claim 19 in which said console display means includes a scalar display of a predetermined original range of values and high limit that is automatically convertible a predetermined number of times by said console microprocessor under program control to a predetermined different range of values and high limit when the next previous high limit is reached.

24. The display of claim 23 in which said scaler display comprises an array of light emitting diodes and associated drivers.

25. The apparatus of claim 19 in which said console has an exterior which sealingly comprises a portion of said console circuitry means, said portion including a plurality of function switches and a screen display, said screen display having means for displaying a plurality of screen images depicting (a) information and (b) options associated with said function switches.

26. The apparatus of claim 25 in which said input means includes input signals representing a selected patient or extracorporeal flow circuit temperature and selected extracorporeal flow circuit pressure and blood flow measurements.

27. The apparatus of claim 26 in which said of screen images depicting information include a MAIN screen displaying information which depends on whether the console is operating on line voltage or the console battery, and if operating on line voltage, then depicting information including:

charge status of said on-board console battery, a histogram of pump flow in units of volume per minute over a period of time ending at current time, and one of a plurality of readouts including instantaneous pump flow (Q), blood flow per a patient weight unit (Q/wt) and blood flow per a patient body surface area unit (Q/BSA), but if operating on the console battery, then depicting information including:

a notice that the battery is in use, charge status of the battery or a projection of battery life or both, and one of a said plurality of readouts including instantaneous pump flow (Q), blood flow per a patient weight unit (Q/wt) and blood flow per a patient body surface area unit (Q/BSA).

28. The apparatus of claim 25 in which said screen images depicting options include a MAIN screen displaying options which depend on whether the apparatus is operating on line voltage or the console battery, and if operating on line voltage, then depicting battery, pressure, flow indices and system options for calling respectively a BATTERY screen, a PRESSURE screen, a FLOW INDICES screen, and a SYSTEM screen, but if operating on the console battery, then depicting pressure, flow indices and system options for calling the PRESSURE screen, the FLOW INDICES screen, and the SYSTEM screen, and an illuminate display option which when the corresponding function switch is keyed illuminates Pressure, Temperature and Timer numerical displays while the switch is keyed plus a predetermined countdown time, then switches off such numerical displays.

29. The apparatus of claim 28 in which said BATTERY screen is called upon keying a function switch operatively associated with the battery option on the MAIN screen, and depicts (a) battery status information including information based on the date of installation of the battery in the console, and (b) main and system options for calling respectively the MAIN or SYSTEM screens.

30. The apparatus of claim 28 in which said PRESSURE screen is called upon keying a function switch operatively associated with the pressure option on the MAIN screen, and depicts at least (a) current calibration values for zero pressure and a high pressure alarms, and (b) pressure alert, zero transducer, main and system options for calling respectively PRESSURE ALERT or ZERO TRANSDUCER screens or said MAIN or SYSTEM screens, and said PRESSURE ALERT screen is called upon keying a function switch operatively associated with the pressure alert option on the PRESSURE screen, and depicts (a) a high pressure alarm value readout, and (b) increase or decrease options for increasing or decreasing said high pressure alarm value, an OK option for accepting a high pressure alarm value, a zero transducer option for calling the ZERO TRANSDUCER screen, and system and main options for calling respectively said SYSTEM or MAIN screens, and said ZERO TRANSDUCER screen is called upon keying a function switch operatively associated with the zero transducer option on the SYSTEM screen, and depicts (a) an open to air zero pressure value readout, and (b) a set zero option for setting the open to air zero pressure value, an OK option for accepting a set open to air zero pressure value, and system and main options for calling respectively said SYSTEM or MAIN screens.

31. The apparatus of claim 28 in which said FLOW INDICES screen is called upon keying a function switch operatively associated with the flow indices option on the MAIN screen, and depicts at least (a) values for height and weight of a patient, and (b) height, weight, Q/wt, Q/BSA and main options for calling respectively HEIGHT, WEIGHT, Q/WT, Q/BSA screens and said MAIN screen, said HEIGHT screen is called upon keying a function switch operatively associated with said height option, and depicts (1) a default patient height value readout, and (2) increase or decrease options for increasing or decreasing said patient height value, an OK option for accepting a selected patient height value, and a main option for calling said MAIN screens;

said WEIGHT screen is called upon keying a function switch operatively associated with said weight option, and depicts (1) a default patient weight value readout, and (2) increase or decrease options for increasing or decreasing said patient weight value, an OK option for accepting a selected patient weight value, and a main option for calling said MAIN screens;

said Q/WT screen is called upon keying a function switch operatively associated with said Q/wt option, and depicts at least (1) said histogram and a Q/wt value readout, and (2) Q/BSA, height, weight, flow indices and main options for calling respectively a Q/BSA screen or said HEIGHT, WEIGHT, FLOW INDICES or MAIN screens, said MAIN screen containing said Q/wt value when called from said Q/WT screen; and said Q/BSA screen is called upon keying a function switch operatively associated with said Q/BSA option, and depicts at least (1) said histogram and a Q/BSA value readout, and (2) height, weight, Q/wt, flow indices and main options for calling respectively said HEIGHT, WEIGHT, Q/WT, FLOW INDICES and MAIN screens, said MAIN screen containing said Q/BSA value when called from said Q/BSA screen.

32. The apparatus of claim 28 in which said SYSTEM screen is called upon keying a function switch operatively associated with the system option on the MAIN screen, and depicts at least (a) said histogram and one of said plurality of Q, Q/wt and Q/BSA readouts, and (b) alarms, status, battery, and main options for calling respectively ALARMS and STATUS screens and said BATTERY and MAIN screens.

33. The apparatus of claim 32 in which said ALARM screen is called upon keying a function switch operatively associated with the alarm option on the SYSTEM screen, the ALARM screen depicting at least (a) said histogram and one of said plurality of Q, Q/wt and Q/BSA readouts, and (b) and low flow alarm, negative flow alarm, alarm volume and main options for calling respectively a LOW FLOW ALARM screen, a NEGATIVE FLOW ALARM screen, an ALARM VOLUME screen, or said MAIN screen, and said LOW FLOW ALARM screen is called upon keying a function switch operatively associated with said low flow alarm option, and depicts (1) a low flow alarm threshold value readout, and (2) increase or decrease options for increasing or decreasing said low flow alarm threshold value, an OK option for accepting a selected low flow alarm threshold value, and system and main options for calling respectively said SYSTEM or MAIN screens;

said NEGATIVE FLOW ALARM screen is called upon keying a function switch operatively associated with said negative flow alarm option, and depicts (1) a negative flow alarm threshold value readout, increase or decrease options for increasing or decreasing low flow alarm threshold values, an OK option for accepting a selected low flow alarm threshold value, and system and main options for calling respectively said SYSTEM or MAIN screens; and said ALARM VOLUME screen is called upon keying a function switch operatively associated with said alarm volume option, and depicts (1) a readout of alarm volume as a percent of maximum, increase or decrease options for increasing or decreasing the percentage of alarm volume maximum, an OK option for accepting a selected alarm volume percentage, and system and main options for calling respectively said SYSTEM or MAIN screens.

34. The apparatus of claim 33 in which said console circuitry means include a connector for a remote computer and:

said STATUS screen is called upon keying a function switch operatively associated with the status option on the SYSTEM screen, and depicts (a) system status readouts including time, date, motor hours, cumulative motor revolutions, battery life and memory capacity of the motor assembly circuit board, and (b) utility, time-date, system and main options for calling respectively a UTILITY screen, a TIME-DATE screen, said SYSTEM screen, and said MAIN screen, and said UTILITY screen is called upon keying a function switch operatively associated with said utility option, and depicts communication, defaults and diagnostics options for calling respectively COMMUNICATION, DEFAULTS and DIAGNOSTICS screens, increase or decrease options for incrementing or decrementing to select one of said communication, defaults and diagnostics options, an OK option for accepting a selected said communication, defaults or diagnostics options, and system and main options for calling respectively said SYSTEM or MAIN screens, and said COMMUNICATION screen is called upon keying a function switch operatively associated with said communication option, and depicts (1) a message to key an associated function switch when ready for a remote computer to receive data transfer from the apparatus, and (2) an OK option for initiating data said transfer, an abort option for canceling data transfer, and utility and main options for calling respectively said UTILITY or MAIN screens, and said DEFAULTS screen is called upon keying a function switch operatively associated with said defaults option, and depicts (a) default value readouts including a default time value for an illuminate display countdown when the apparatus is operating on the console battery and a default high pressure alarm value and (b) illuminate display countdown default and high pressure alarm default options for calling respectively an ILLUMINATE DISPLAY COUNTDOWN DEFAULT screen and a HIGH PRESSURE ALARM DEFAULT screen, increase or decrease options for incrementing or decrementing to select one of said illuminate display countdown default or high pressure alarm default options, an OK option for accepting a selected default option, and utility and main options for calling respectively said UTILITY or MAIN screens, and said ILLUMINATE DISPLAY COUNTDOWN DEFAULT screen is called upon keying a function switch operatively associated with said illuminate display countdown default option, and depicts (a) a default time value readout for said illuminate display countdown, increase or decrease options for increasing or decreasing said default time value, an OK option for accepting a selected default time value for said illuminate display countdown, a more option for calling a MORE screen, and utility and main options for calling respectively said UTILITY or MAIN screens, and said HIGH PRESSURE ALARM DEFAULT screen is called upon keying a function switch operatively associated with said high pressure alarm default option, and depicts (a) a default high pressure alarm readout for high pressure alarm, increase or decrease options for increasing or decreasing said default high pressure alarm, an OK option for accepting a selected default high pressure alarm, a more option for calling a MORE screen, and utility and main options for calling respectively said UTILITY or MAIN screens, and said MORE screen is called upon keying a function switch operatively associated with said more option, and depicts (a) default value readouts including a default low flow alarm value and a default negative flow alarm value and (b) low flow alarm default and negative flow alarm default options for calling respectively an a LOW FLOW ALARM DEFAULT screen and a NEGATIVE FLOW ALARM DEFAULT screen, increase or decrease options for incrementing or decrementing to select one of said low flow alarm default or negative flow alarm default options, an OK option for accepting a selected such default option, and utility and main options for calling respectively said UTILITY or MAIN screens, and said TIME-DATE screen is called upon keying a function switch operatively associated with said time-date option, and depicts, and depicts (a) readouts including a time of day value and a date and (b) time and date options for calling respectively an TIME screen and a DATE screen, increase or decrease options for incrementing or decrementing to select one of said time or date options, an OK option for accepting a selected time or date option, and system and main options for calling respectively said SYSTEM or MAIN screens, and said TIME screen is called upon keying a function switch operatively associated with said time option, and depicts (a) a time of day readout, increase or decrease options for increasing or decreasing said time of day readout, an OK option for accepting a selected time of day, and system and main options for calling respectively said SYSTEM or MAIN screens, and said DATE screen is called upon keying a function switch operatively associated with said date option, and depicts (a) a date readout, increase or decrease options for increasing or decreasing said date readout, an OK option for accepting a selected date, and system and main options for calling respectively said SYSTEM or MAIN screens.

35. The apparatus of claim 15 wherein said console microprocessor under program control further comprises means requiring said speed selector means to be set to zero before said motor can be rotated.

36. The apparatus of claim 15 in which said console microprocessor under program control further includes means for inputting a minimum speed at which said console microprocessor means under program control will instruct said motor microprocessor to ignore a said selected speed signal lower than said minimum speed and said console microprocessor will generate an alert signal that the said selected speed is lower than the minimum speed.

37. The apparatus of claim 36 further comprising means controllable by an operator after said alert signal is generated for permitting the console microprocessor under program control to instruct the motor microprocessor to produce the control signal at said selected speed signal lower than said minimum speed until motor speed is reset above said minimum speed or electrical power to said motor housing circuitry is discontinued.

38. The apparatus of claim 15 in which said power means in said console includes:
a power cord for receiving AC power, and
power supply means electrically connected to said console circuitry and said power cord for converting AC line voltage to DC voltage.

39. The apparatus of claim 38 in which
said console includes at least one on-board DC battery and a connector for an external DC power source both connected to said console circuitry, and in which
said console microprocessor under program control further comprises:
means for determining what power is available from the console power sources comprising said power supply means, said on-board DC battery and said external DC power source connector, and if AC power is available, determines whether it is 240V, 120V or 90V, and for auto-configuring the power supply means to accept the power available,
means for prioritizing and distributing power such that if DC power is available from said console power supply means, it has priority, but if DC power is not available from said console power supply means and external DC power from said console external DC power source connector is available, then it has priority, but if both DC power from said console power supply means and from said console external DC power source connector are not available, then said on-board console battery has priority, and
means for trickle charging said on-board console battery when DC power from said console power supply means is available.

40. Apparatus which comprises:
a motor housing,
motive means in said motor housing adapted to connect to a centrifugal pump to rotationally drive the centrifugal blood pump, said motive means including a motor for rotationally driving the centrifugal blood pump and a controller operatively associated with said motor for controlling the rotational speed of said motor, sensor means operatively associated with said motive means for sensing the rotational speed of the motive means and outputting a monitor signal signifying such rotational speed, a console separate from said motor housing, speed selector means in said console for generating a selected speed signal signifying a selected rotational speed for said motor, motor housing program memory in said motor housing for storage of a program of microprocessor readable instructions, motor housing microprocessor in said motor housing in electrical connection with said program memory, said controller, and said speed selector means, and under program control of said motor-housing program memory, for receiving said selected speed signal and generating a speed control signal to the controller signifying the selected speed for the controller, console program memory in said console for storage of a program of microprocessor readable instructions, console microprocessor in said console in electrical connection with said console program memory, said speed selector means, said sensor means, and said motor housing microprocessor, and under program control of said console program memory, for receiving said speed signal and said monitor signal and determining whether the monitor signal is within a predetermined limit of allowable variance of the speed signal, and
if within the allowable limit, then outputting a display signal, but
if outside the allowable limit under a predetermined sampling protocol, then outputting an alarm signal, display means in said motor housing in electrical communication with said console microprocessor and responsive to said display signal for displaying information, power means in said console for supplying a source of DC power, and circuitry means in said motor housing and in said console and electrically conductive cable means interconnecting said circuitry means for transmission of DC power to said motor housing circuitry means from said console power means and for providing electrical communication between said speed selector means, said program memory and said console microprocessor and said motor housing microprocessor means, said controller, said sensor means, and said display means, said circuitry means of said console further including:
input means adapted to receive one or more input signals from one or more peripheral signaling sources adapted to sense a parameter of a patient connected in a blood flow circuit having an extracorporeal flow portion including a centrifugal blood pump, or a parameter of the extracorporeal portion of said circuit, or both,
said console microprocessor under program control further including:
means for interpreting said input signals from said one or more peripheral signaling sources and for outputting display signals to said console display means to display information based on said input signals,
said console having an exterior which sealingly comprises a portion of said console circuitry means, said portion including a plurality of function switches and a screen display, said screen display having means for displaying a plurality of screen images depicting (a) information and (b) options associated with said function switches,
said screen images depicting options include a MAIN screen displaying options which depend on whether the apparatus is operating on line voltage or the console battery, and
if operating on line voltage, then depicting battery, pressure, flow indices and system options for calling respectively a BATTERY screen, a PRESSURE screen, a FLOW INDICES screen, and a SYSTEM screen, but
if operating on the console battery, then depicting pressure, flow indices and system options for calling the PRESSURE screen, the FLOW INDICES screen, and the SYSTEM screen, and an illuminate display option which when the corresponding function switch is keyed illuminates Pressure, Temperature and Timer numerical displays while the switch is keyed plus a predetermined countdown time, then switches off such numerical displays,
wherein said PRESSURE screen is called upon keying a function switch operatively associated with the pressure option on the MAIN screen, and depicts at least (a) current calibration values for zero pressure and a high pressure alarms, and (b) pressure alert, zero transducer, main and system options for calling respectively PRESSURE ALERT or ZERO TRANSDUCER screens or said MAIN or SYSTEM screens, and
said PRESSURE ALERT screen is called upon keying a function switch operatively associated with the pressure alert option on the PRESSURE screen, and depicts (a) a high pressure alarm value readout, and (b) increase or decrease options for increasing or decreasing said high pressure alarm value, an OK option for accepting a high pressure alarm value, a zero transducer option for calling the ZERO TRANSDUCER screen, and system and main options for calling respectively said SYSTEM or MAIN screens, and
said ZERO TRANSDUCER screen is called upon keying a function switch operatively associated with the zero transducer option on the SYSTEM screen, and depicts (a) an open to air zero pressure value readout, and (b) a set zero option for setting the open to air zero pressure value, an OK option for accepting a set open to air zero pressure value, and system and main options for calling respectively said SYSTEM or MAIN screens.

41. The apparatus of claim 40 in which
said FLOW INDICES screen is called upon keying a function switch operatively associated with the flow indices option on the MAIN screen, and depicts at least (a) values for height and weight of a patient, and (b) height, weight, Q/wt, Q/BSA and main options for calling respectively HEIGHT, WEIGHT, Q/WT, Q/BSA screens and said MAIN screen,
said HEIGHT screen is called upon keying a function switch operatively associated with said height option, and depicts (1) a default patient height value readout, and (2) increase or decrease options for increasing or decreasing said patient height value, an OK option for accepting a selected patient height value, and a main option for calling said MAIN screens;
said WEIGHT screen is called upon keying a function switch operatively associated with said weight option, and depicts (1) a default patient weight value readout, and (2) increase or decrease options for increasing or decreasing said patient weight value, an OK option for accepting a selected patient weight value, and a main option for calling said MAIN screens;

said Q/WT screen is called upon keying a function switch operatively associated with said Q/wt option, and depicts at least (1) said histogram and a Q/wt value readout, and (2) Q/BSA, height, weight, flow indices and main options for calling respectively a Q/BSA screen or said HEIGHT, WEIGHT, FLOW INDICES or MAIN screens, said MAIN screen containing said Q/wt value when called from said Q/WT screen; and said Q/BSA screen is called upon keying a function switch operatively associated with said Q/BSA option, and depicts at least (1) said histogram and a Q/BSA value readout, and (2) height, weight, Q/wt, flow indices and main options for calling respectively said HEIGHT, WEIGHT, Q/WT, FLOW INDICES and MAIN screens, said MAIN screen containing said Q/BSA value when called from said Q/BSA screen.

42. The apparatus of claim 41 wherein said data recording means comprises volatile memory and a DC battery to provide power to said motor housing volatile memory when power from an external source is absent.

43. The apparatus of claim 40 in which said SYSTEM screen is called upon keying a function switch operatively associated with the system option on the MAIN screen, and depicts at least (a) said histogram and one of said plurality of Q, Q/wt and Q/BSA readouts, and (b) alarms, status, battery, and main options for calling respectively ALARMS and STATUS screens and said BATTERY and MAIN screens.

44. The apparatus of claim 43 in which said ALARM screen is called upon keying a function switch operatively associated with the alarm option on the SYSTEM screen, the ALARM screen depicting at least (a) said histogram and one of said plurality of Q, Q/wt and Q/BSA readouts, and (b) and low flow alarm, negative flow alarm, alarm volume and main options for calling respectively a LOW FLOW ALARM screen, a NEGATIVE FLOW ALARM screen, an ALARM VOLUME screen, or said MAIN screen, and said LOW FLOW ALARM screen is called upon keying a function switch operatively associated with said low flow alarm option, and depicts (1) a low flow alarm threshold value readout, and (2) increase or decrease options for increasing or decreasing said low flow alarm threshold value, an OK option for accepting a selected low flow alarm threshold value, and system and main options for calling respectively said SYSTEM or MAIN screens;

said NEGATIVE FLOW ALARM screen is called upon keying a function switch operatively associated with said negative flow alarm option, and depicts (1) a negative flow alarm threshold value readout, increase or decrease options for increasing or decreasing low flow alarm threshold values, an OK option for accepting a selected low flow alarm threshold value, and system and main options for calling respectively said SYSTEM or MAIN screens; and said ALARM VOLUME screen is called upon keying a function switch operatively associated with said alarm volume option, and depicts (1) a readout of alarm volume as a percent of maximum, increase or decrease options for increasing or decreasing the percentage of alarm volume maximum, an OK option for accepting a selected alarm volume percentage, and system and main options for calling respectively said SYSTEM or MAIN screens.

45. The apparatus of claim 44 in which said console circuitry means include a connector for a remote computer and:

said STATUS screen is called upon keying a function switch operatively associated with the status option on the SYSTEM screen, and depicts (a) system status readouts including time, date, motor hours, cumulative motor revolutions, battery life and memory capacity of the motor assembly circuit board, and (b) utility, time-date, system and main options for calling respectively a UTILITY screen, a TIME-DATE screen, said SYSTEM screen, and said MAIN screen, and said UTILITY screen is called upon keying a function switch operatively associated with said utility option, and depicts communication, defaults and diagnostics options for calling respectively COMMUNICATION, DEFAULTS and DIAGNOSTICS screens, increase or decrease options for incrementing or decrementing to select one of said communication, defaults and diagnostics options, an OK option for accepting a selected said communication, defaults or diagnostics options, and system and main options for calling respectively said SYSTEM or MAIN screens, and said COMMUNICATION screen is called upon keying a function switch operatively associated with said communication option, and depicts (1) a message to key an associated function switch when ready for a remote computer to receive data transfer from the apparatus, and (2) an OK option for initiating data said transfer, an abort option for canceling data transfer, and utility and main options for calling respectively said UTILITY or MAIN screens, and said DEFAULTS screen is called upon keying a function switch operatively associated with said defaults option, and depicts (a) default value readouts including a default time value for an illuminate display countdown when the apparatus is operating on the console battery and a default high pressure alarm value and (b) illuminate display countdown default and high pressure alarm default options for calling respectively an ILLUMINATE DISPLAY COUNTDOWN DEFAULT screen and a HIGH PRESSURE ALARM DEFAULT screen, increase or decrease options for incrementing or decrementing to select one of said illuminate display countdown default or high pressure alarm default options, an OK option for accepting a selected default option, and utility and main options for calling respectively said UTILITY or MAIN screens, and said ILLUMINATE DISPLAY COUNTDOWN DEFAULT screen is called upon keying a function switch operatively associated with said illuminate display countdown default option, and depicts (a) a default time value readout for said illuminate display countdown, increase or decrease options for increasing or decreasing said default time value, an OK option for accepting a selected default time value for said illuminate display countdown, a more option for calling a MORE screen, and utility and main options for calling respectively said UTILITY or MAIN screens, and said HIGH PRESSURE ALARM DEFAULT screen is called upon keying a function switch operatively associated with said high pressure alarm default option, and depicts (a) a default high pressure alarm readout for high pressure alarm, increase or decrease options for increasing or decreasing said default high pressure alarm, an OK option for accepting a selected default high pressure alarm, a more option for calling a MORE screen, and utility and main options for calling respectively said UTILITY or MAIN screens, and said MORE screen is called upon keying a function switch operatively associated with said more option, and depicts (a) default value readouts including a default low flow alarm value and a default negative flow alarm value and (b) low flow alarm default and negative flow alarm default options for calling respectively an a LOW FLOW ALARM DEFAULT screen and a NEGATIVE FLOW ALARM DEFAULT screen, increase or decrease options for incrementing or decrementing to select one of said low flow alarm default or negative flow alarm default options, an OK option for accepting a selected such default option, and utility and main options for calling respectively said UTILITY or MAIN screens, and said TIME-DATE screen is called upon keying a function switch operatively associated with said time-date option, and depicts, and depicts (a) readouts including a time of day value and a date and (b) time and date options for calling respectively an TIME screen and a DATE screen, increase or decrease options for incrementing or decrementing to select one of said time or date options, an OK option for accepting a selected time or date option, and system and main options for calling respectively said SYSTEM or MAIN screens, and said TIME screen is called upon keying a function switch operatively associated with said time option, and depicts (a) a time of day readout, increase or decrease options for increasing or decreasing said time of day readout, an OK option for accepting a selected time of day, and system and main options for calling respectively said SYSTEM or MAIN screens, and said DATE screen is called upon keying a function switch operatively associated with said date option, and depicts (a) a date readout, increase or decrease options for increasing or decreasing said date readout, an OK option for accepting a selected date, and system and main options for calling respectively said SYSTEM or MAIN screens.

* * * * *